(12) United States Patent
Plass

(10) Patent No.: US 10,376,256 B2
(45) Date of Patent: Aug. 13, 2019

(54) WOUND OCCLUSION DEVICE

(71) Applicant: Plass Medtech AG, Stetten (CH)

(72) Inventor: André Plass, Zurich (CH)

(73) Assignee: Plass Rescue Technologies AG, Stetten (CH)

( * ) Notice: Subject to any disclaimer, the term of this patent is extended or adjusted under 35 U.S.C. 154(b) by 296 days.

(21) Appl. No.: 15/310,554

(22) PCT Filed: May 12, 2015

(86) PCT No.: PCT/EP2015/060518
§ 371 (c)(1),
(2) Date: Nov. 11, 2016

(87) PCT Pub. No.: WO2015/173264
PCT Pub. Date: Nov. 19, 2015

(65) Prior Publication Data
US 2017/0079632 A1    Mar. 23, 2017

(30) Foreign Application Priority Data
May 12, 2014    (CH) .......................................... 711/14

(51) Int. Cl.
*A61B 17/08*    (2006.01)
*A61B 17/00*    (2006.01)

(52) U.S. Cl.
CPC .................... *A61B 17/0057* (2013.01); *A61B 2017/00592* (2013.01); *A61B 2017/00597* (2013.01);
(Continued)

(58) Field of Classification Search
CPC ..... A61B 17/00; A61B 17/10; A61B 17/0057; A61B 2017/00867; A61B 2017/00592;
(Continued)

(56) References Cited

U.S. PATENT DOCUMENTS 3,874,388 A    4/1975    King et al.
7,708,751 B2 *    5/2010    Hughes .................. A61B 5/055
                                                                606/172
(Continued)

FOREIGN PATENT DOCUMENTS

RU    2404823 C2    11/2010
WO    96/32882 A1    10/1996
WO    2011/106713 A2    9/2011

OTHER PUBLICATIONS

PCT/EP2015/060518 filed May 12, 2015 International Search Report and Written Opinion dated Oct. 22, 2015.

*Primary Examiner* — Vi X Nguyen
(74) *Attorney, Agent, or Firm* — Rutan & Tucker, LLP

(57) ABSTRACT

Wound occlusion devices and methods for acute treatment of massively bleeding external wounds are described. The wound occlusion devices may include a base element, a sealing element, and a release mechanism. The sealing element may be configured to transform between a contracted configuration and an expanded configuration by the release mechanism. The expanded configuration of the sealing element may be adaptable to the shape of a wound W, forming a form-locked and/or force-locked connection with the wound W. The form-locked and/or force-locked connection of the sealing element with the wound W may provide an occlusion function.

35 Claims, 20 Drawing Sheets

(52) U.S. Cl.
CPC ............... *A61B 2017/00632* (2013.01); *A61B 2017/00654* (2013.01); *A61B 2017/00867* (2013.01); *A61B 2017/00893* (2013.01)

(58) Field of Classification Search
CPC ........... A61B 2017/00893; A61B 2017/00632; A61B 17/08; A61B 2017/00637; A61B 2017/00654
See application file for complete search history.

(56) References Cited

U.S. PATENT DOCUMENTS

| | | |
|---|---|---|
| 2011/0082495 A1 | 4/2011 | Ruiz |
| 2011/0144661 A1 | 6/2011 | Houser et al. |
| 2011/0213449 A1* | 9/2011 | Ginn .................. A61B 17/0057 623/1.11 |

* cited by examiner

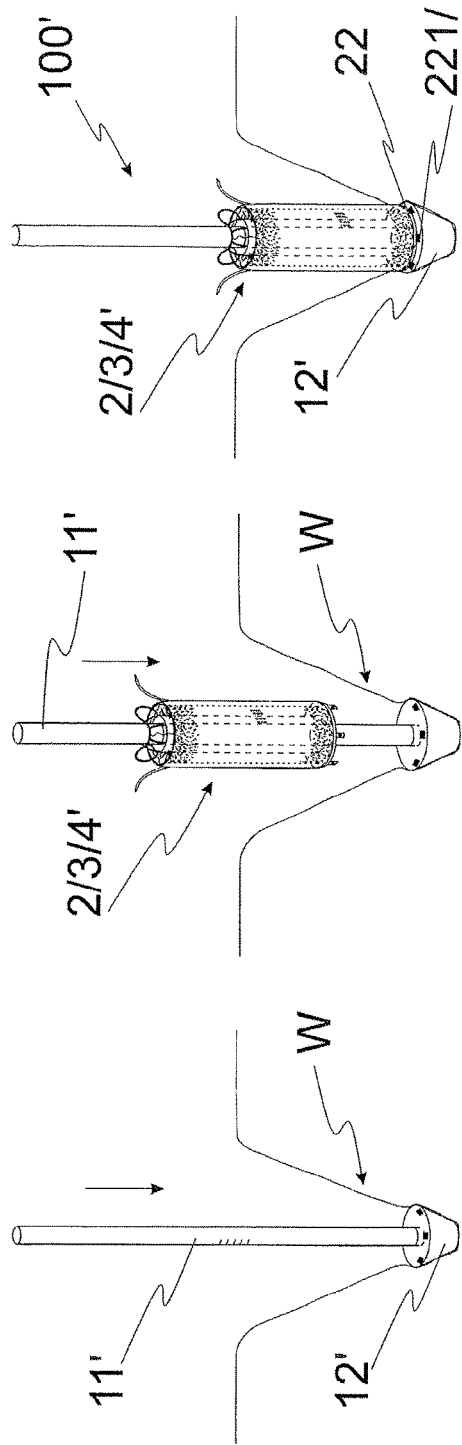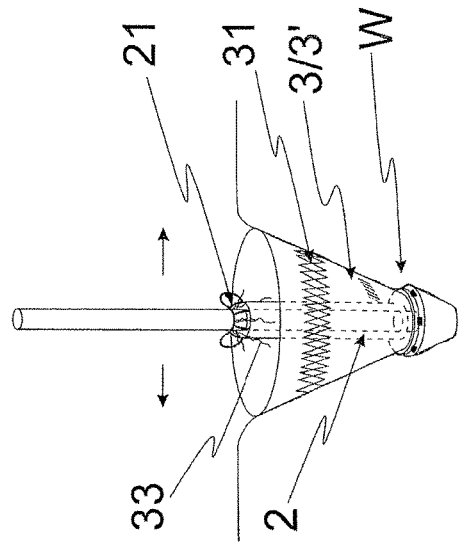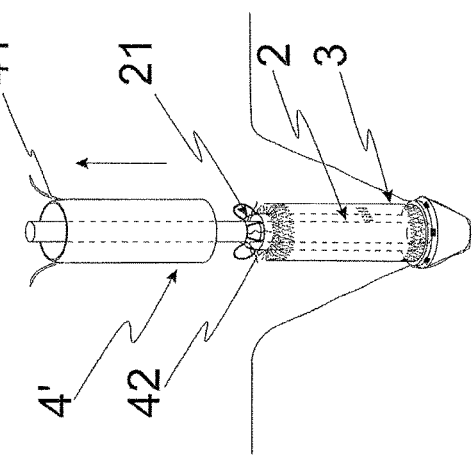

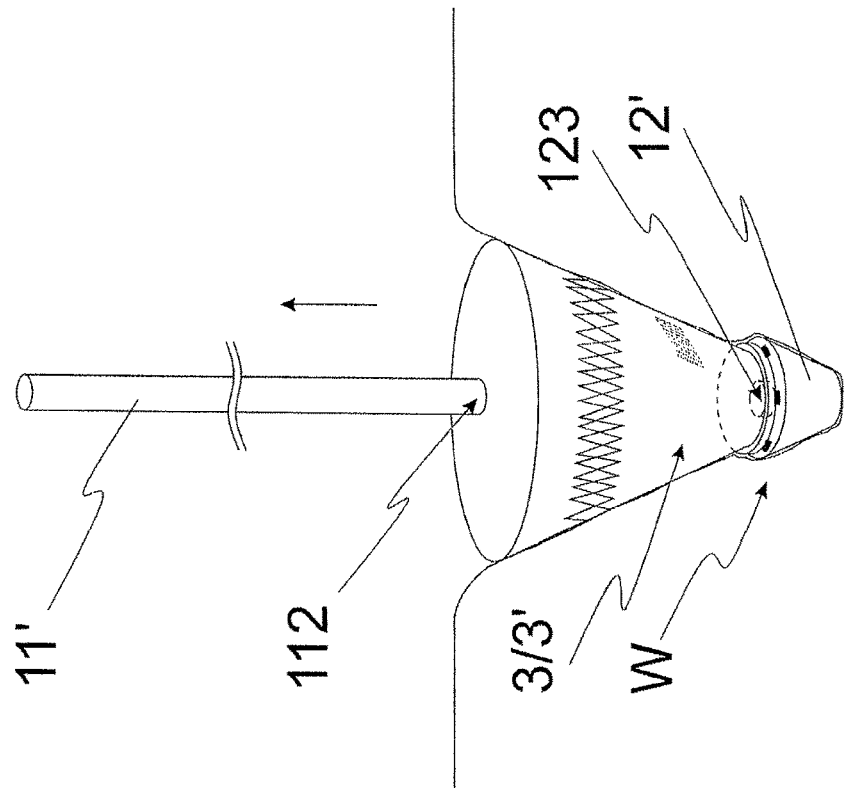
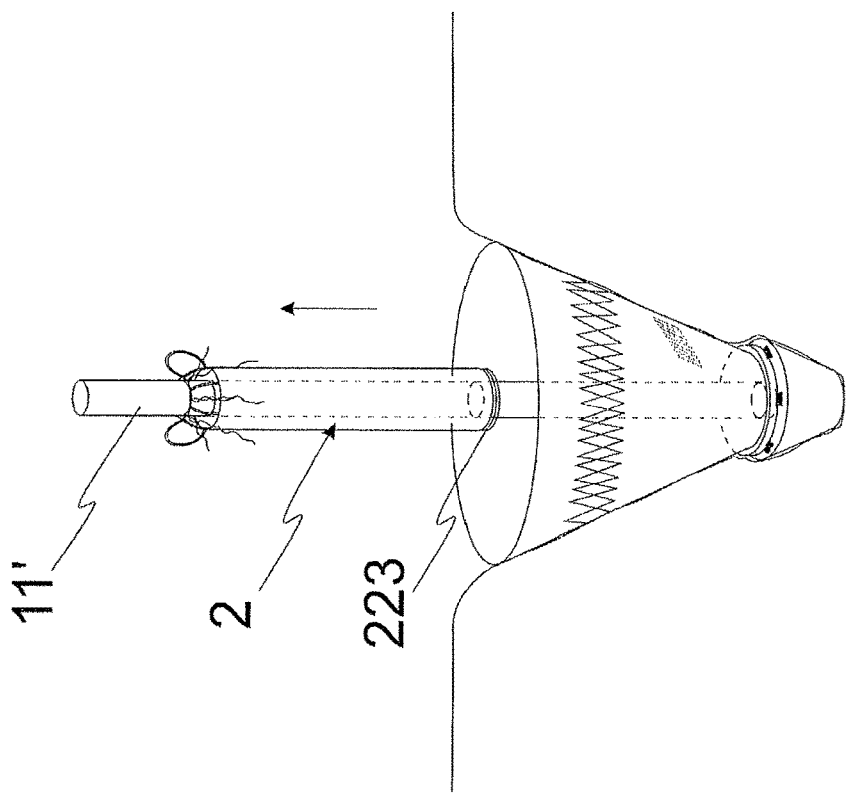

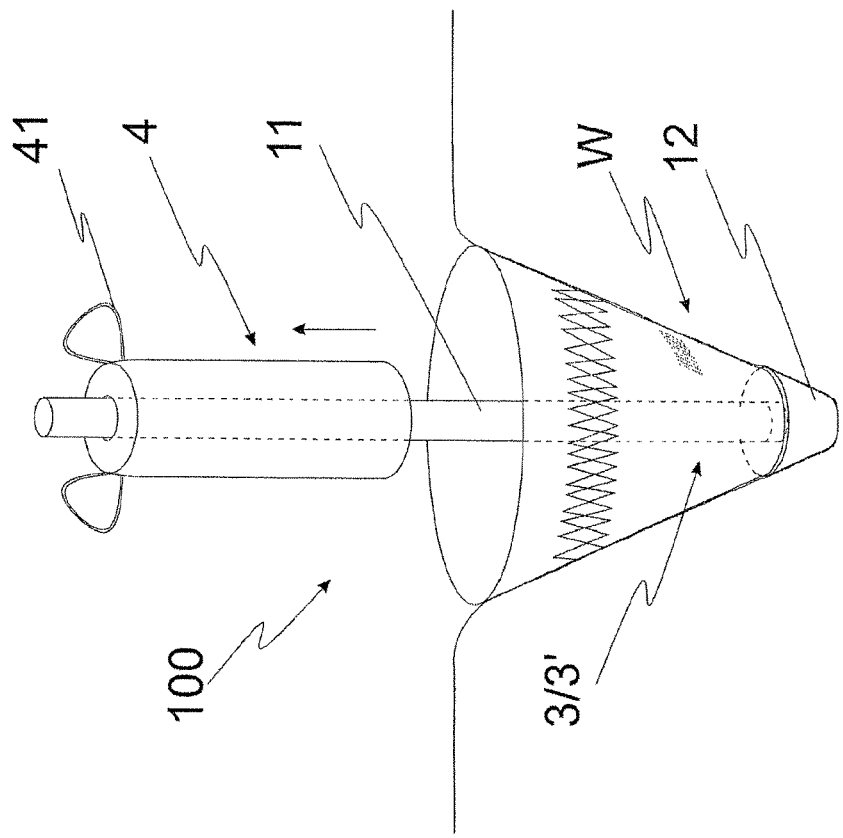
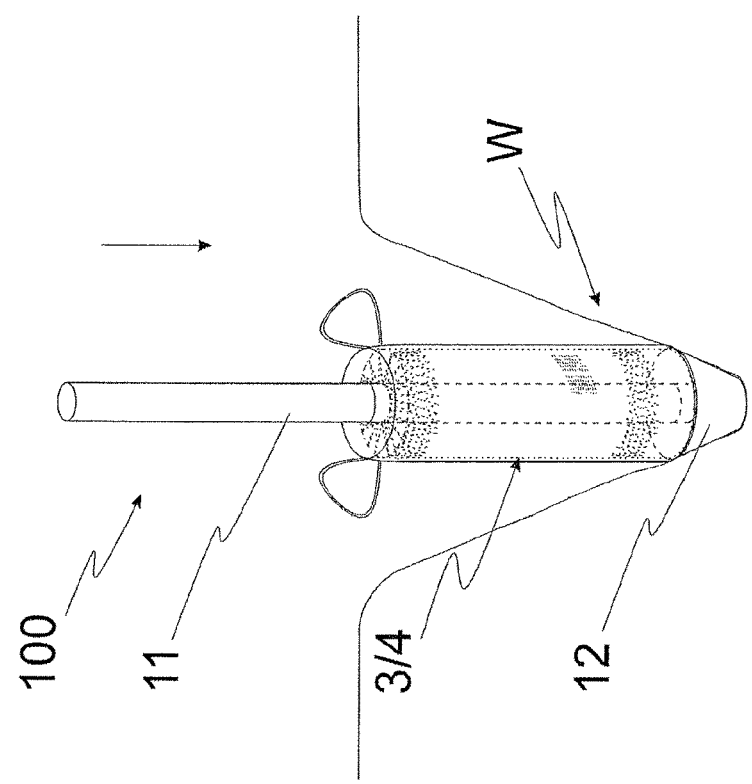

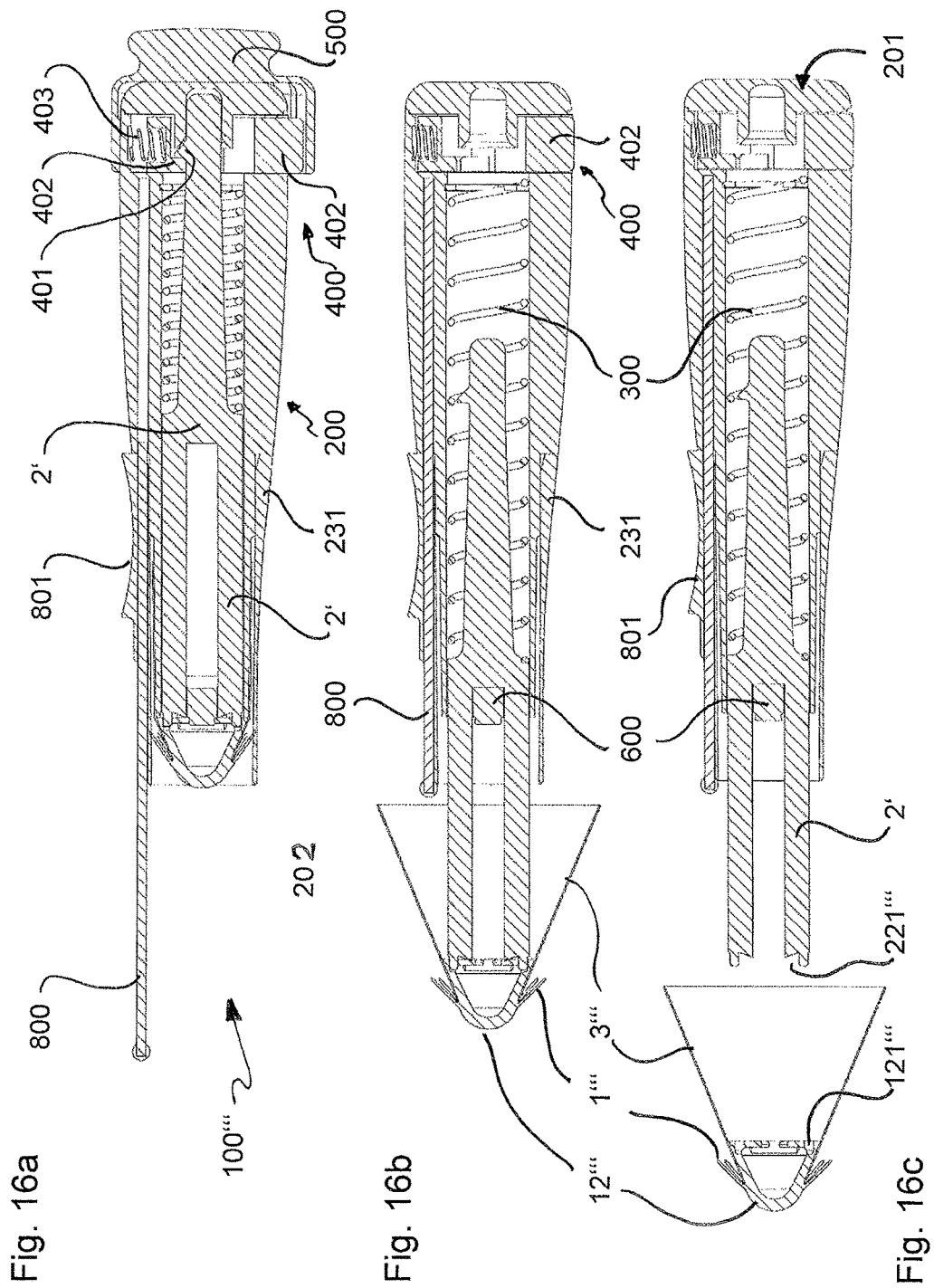

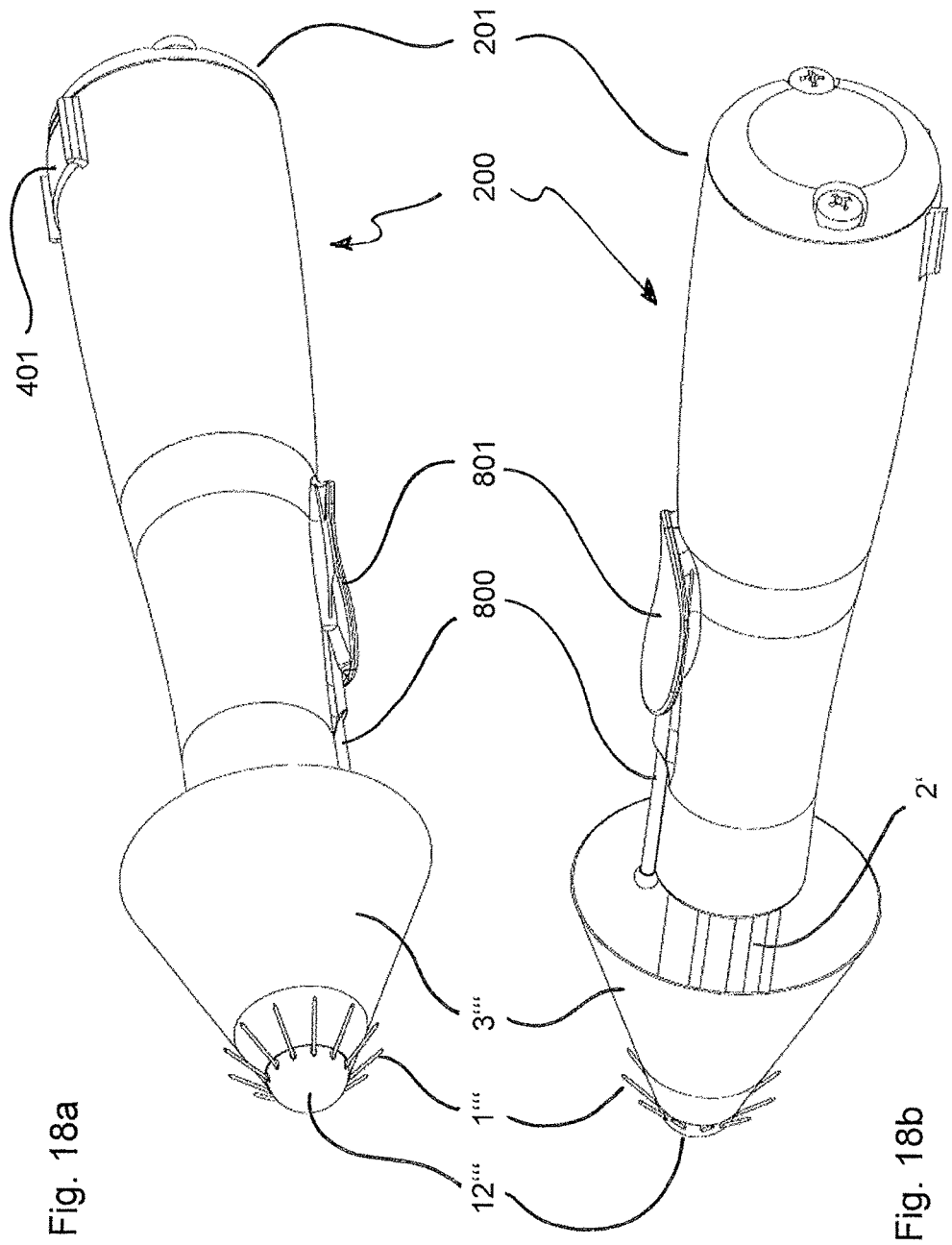

WOUND OCCLUSION DEVICE

PRIORITY

This application is a U.S. national stage application under 35 USC § 371 of International Application No. PCT/EP2015/060518, filed May 12, 2015, which claims priority to Switzerland Patent Application No. 00711/14, filed May 12, 2014, each of which is incorporated by reference in its entirety into this application.

TECHNICAL FIELD

The present invention relates to devices and methods for the acute treatment of massively bleeding external wounds.

BACKGROUND

Uncontrolled bleeding of external wounds is a common problem resulting in death after injuries. In particular, haemorrhage after combat injuries is a leading cause of mortality of the soldiers on the battlefield. According to the Armed Forces Medical Examiner Service Mortality Surveillance Division, 90.9% of the potentially survivable battlefield fatalities that occurred in the pre-medical treatment facility environment during the Operation Iraqi Freedom and Operation Enduring Freedom between October 2001 and June 2011 were associated with haemorrhage. Thus, the necessity of onsite acute mitigation or termination of the haemorrhage in the prehospital environment is undisputed.

Commonly, the acute way to treat bleeding external wounds consists of the application of pressure dressings directly onto the injured soft tissue to mitigate, or, rarely to terminate the acute bleeding of the burst vessels, especially arteries. The pressure dressings are, however, inadequate and inflexible to adapt sufficiently to the specific wound cavity and in addition often insufficient to stop bleeding due to the difficulties to hold the dressings in the wound. Moreover, the frequent necessity of repeated change of the wound dressing increases the risk for infection, which aggravates the scenario.

US2012/0209232 A1 describes a haemostatic composition comprising a plurality of liquid-expandable articles of absorbent material disposed on a backing material. When delivered into the wound, the liquid-expandable articles are adapted to expand upon contact with a liquid, for example blood, thereby to fill the wound cavity and control the haemorrhage. Means for the controlled removal of the expanded articles at the hospital prior to any surgical intervention are not specified, where uncontrolled removal of the ensemble of the expanded articles and the clotted blood could lead to additional damages in the wound. In addition, the accessibility of every sector of the wound cavity in cases of deep and narrow wound shapes remains unspecified.

DISCLOSURE OF THE INVENTION

It is an object of the present invention to provide a device for a simple, controllable and acute treatment of massively bleeding external wounds. It is a further object of the present invention to provide a method for a simple, controllable and acute treatment of massively bleeding external wounds.

In this document, terms indicating a direction or orientation, such as "left", "right", "top", "bottom" are exclusively intended to aid the reader's understanding in combination with the figures. They do not imply any specific directions and/or orientations for the application.

These objects are achieved by a wound occlusion device and a wound occlusion method according to the independent claims. Some favourable embodiments are defined by the dependent claims.

According to a first aspect of the invention, the object is achieved by providing a wound occlusion device, also named Acute Wound Occluder. It comprises an ensemble of a base element, a sealing element and a release mechanism of the sealing element. The sealing element may comprise a frame element and a layer element. The sealing element has a contracted configuration and an expanded configuration, and can be transformed between the two configurations. The expanded configuration may be achieved by the release mechanism as soon as the wound occlusion device is placed into the wound. In the expanded configuration, the sealing element may adapt to the shape of the wound forming a form-locked and/or force-locked connection with the wound and thereby providing an occlusion of the bleeding wound, especially of the ruptured blood vessels. In addition the occluded wound is protected from further contamination or infection.

The novel Acute Wound Occluder is very easy to use, even at night and/or under combat conditions. In it's simplest forms it can even be applied one-handed. It can be used by non-medical personnel with no or minimal medical training.

The base element may serve to anchor the wound occlusion device in the wound by positioning the base element at the base of the wound. In an embodiment, the base element is made of a skid-proof material, which may be rubber. In a further embodiment, the base element is of conical shape. In another embodiment, the base element has a ribbed surface. The specific shape of the base element may support first acute occlusion of the contact region between the base element and the wound when applied into the wound. Applied force on the base element may support the first acute occlusion of the wound by the base element.

In another embodiment, the base element is made of and/or covered by a blood-proof and/or water-proof material, which may be polytetrafluorethylen (PTFE) and/or a haemostatic material supporting coagulation, which may be Nu-Knit (Ethicon Inc., http://www.ethicon360.com/products/ethicon-biosurgery). The specific material composition and/or coverage of the base element may support the occlusion of the wound at the contact region between the base element and the wound.

In an embodiment, the frame element is a coil. In another embodiment, the frame element is a wire braiding. In a further embodiment, the frame element is made of a shape-memory material, as for example Nitinol.

The layer element may be, according to a preferred embodiment, made of and/or covered by a blood-proof and/or water-proof material, which may be polytetrafluorethylen (PTFE). Preferably, the layer element may be made of and/or covered by a haemostatic material supporting coagulation, which may be Nu-Knit. In a preferred embodiment, the layer element may be covered by an antibacterial and/or antibiotic material, which may be GentaFleece (Producer: Baxter, http://www.ecomm.baxter.com).

The sealing element is transformable between a contracted and an expanded configuration. The expanded configuration may be achieved by the use of a release mechanism, which may comprise springs, and/or self-expansion exploiting the shape-memory material of the frame element. The springs may support a force-locked and/or form-locked connection of the sealing element within the wound. In an embodiment, a balloon inlay may support the force-locked and/or form-locked connection of the sealing element with the wound. According to a preferred embodiment, the sealing element may assume a funnel-like or tent-like shape in the expanded configuration. Preferably, the sealing element, in the expanded configuration, may adapt to the shape of the wound exploiting for example the characteristics of the shape-memory material of the frame element, resulting in a form-locked and/or force-locked connection with the wound. The temperature of the wound tissue and/or the blood may additionally support the adaptation of the sealing element to the shape of the wound. Together with the haemostatic properties of the layer element, the form-locked and/or force-locked connection of the sealing element with the wound may result in mitigation and/or termination of the bleeding and provide the acute occlusion of the wound.

In an embodiment, the sealing element is covered by a removable sheath element in its contracted configuration. The sheath element may be made of a plastic material. The sheath element may be retained to the sealing element by a pre-load force of the contracted configuration of the sealing element and/or of the release mechanism of the sealing element. In another embodiment, the sheath element may be releasably coupled to elements of the wound occlusion device by a sheath coupling mechanism which may comprise releasable spring elements and/or hook elements and mechanisms to release the coupling. The removal of the sheath element may trigger the release mechanism of the sealing element. In a preferred embodiment, the sheath element comprises at least one handle coupled to a top portion of the sheath element. The handles may enable to hold and to guide the sheath element by the fingers of the user of the wound occlusion device.

The wound occlusion device may, in an embodiment, comprise a retain apparatus which may be used to retain the wound occlusion device in the wound during steps of application and/or removal of elements of the wound occlusion device. The retain apparatus may comprise a deploy mechanism that is arranged such that the retain apparatus may be deployed at a specific step of the application of the wound occlusion device. The deploy mechanism may be reversible, such that the retain apparatus may be retracted at a specific step of the application and/or removal of the wound occlusion device.

In an embodiment, the retain apparatus may comprise at least one hook element at a bottom portion of the wound occlusion device or at the base element. In another embodiment, the retain apparatus may comprise at least one spring element at a bottom portion of the wound occlusion device or at the base element. The retain apparatus may be deployed, in an embodiment, at a removal step of the sheath element, the removal of the sheath element providing the deploy mechanism of the retain apparatus.

In a further embodiment, the retain apparatus comprises a rod-like bar element. The bar element may be releasably coupled to the base element. The coupling may comprise screw joints or bayonet joints or other fitting means. Applied force on the bar element may be used to retain the wound occlusion device in the wound during steps of the application and/or the removal of elements of the wound occlusion device.

According to a preferred embodiment, the bar element has a circular cross-section. Other embodiments comprise bar elements with other geometries such as bar elements with triangular, rectangular, hexagonal or other cross-sections.

The bar element may have, according to a preferred embodiment, at least twice the length of the sealing element and/or of the sheath element.

The sealing element may be coupled to at least a portion of the bar element and/or of the base element. In a preferred embodiment, the sealing element, in the contracted configuration, encompasses the bar element. In a further embodiment, the sealing element is fixed at a bottom portion of the bar element or at the base element and is releasably coupled to a top portion of the bar element. The coupling to the top portion of the bar element may comprise severable strands. The expanded configuration of the sealing element may be achieved by severing said strands which may trigger the release mechanism of the sealing element.

According to another embodiment, the wound occlusion device may comprise a carrier element that is movable on the bar element. The carrier element may be delivered into the wound by movement on the bar element. In a further embodiment, the carrier element has a tubular shape, with the bar element being receivable in the carrier element. The bar element may have, according to a preferred embodiment, at least twice the length of the carrier element. The carrier element may be made of a plastic material.

In an embodiment, the bottom portion of the carrier element comprises a releasably coupled bottom ring with the bar element being receivable in said bottom ring. The bottom ring may be coupled to the carrier element by screw joints or bayonet joints or other fitting means.

The carrier element may be coupled to the base element by mutually matching connector portions comprised in both the bottom portion of the carrier element, which may comprise said bottom ring, and the base element and which connector portions may comprise parts of screw joints or parts of bayonet joints or other fitting means.

In an embodiment, at least one handle is attached on the top portion of the carrier element, which may comprise a top ring assembly. The top ring assembly may comprise a top ring and struts, with the bar element being receivable in said top ring. The handles may enable to hold and to guide the carrier element by the fingers of the user of the wound occlusion device.

According to an aspect of the present invention, the sealing element is coupled to at least a portion of the carrier element and thus delivered together with the carrier element into the wound by the movement of the carrier element on the bar element.

In an embodiment, the sealing element is fixed at the bottom portion of the carrier element and is releasably coupled to the top portion of the carrier element, which top portion may comprise the top ring assembly. The coupling to the top portion of the carrier element may comprise severable strands. The expanded configuration of the sealing element may be achieved by severing said strands which may trigger the release mechanism of the sealing element.

According to a preferred embodiment, the ensemble of the carrier element and the sealing element is covered by a removable sheath element. In an embodiment, the sheath element is coupled to the top portion of the carrier element by severable strands. In another embodiment, the sheath element may be retained to the ensemble of the carrier element and the sealing element by a pre-load force of the contracted configuration of the sealing element and/or of the release mechanism of the sealing element. In a further embodiment, the sheath element may be releasably coupled to elements of the wound occlusion device by a sheath coupling mechanism which may comprise releasable spring elements and/or hook elements and mechanisms to release the coupling. The removal of the sheath element may trigger the release mechanism of the sealing element.

In a further embodiment, the wound occlusion device comprises additional dispensing means coupled and/or comprised in the bar element and/or the base element and/or the carrier element and/or the sealing element for the dispensing of various drugs in to the wound. The dispensing means, according to a further embodiment, may comprise a cannula.

In an embodiment, the wound occlusion device may comprise a metering apparatus. The metering apparatus may be used to determine the spatial dimensions, preferably the depth, of the wound before application of the occlusion device. In an embodiment, the metering apparatus comprises a measurement scale. In the simplest case, the metering apparatus may be used to determine at least the depth of the wound.

In an embodiment, the bar element comprises the metering apparatus which may be a measurement scale. The measurement scale may comprise a scale and/or visible ticks on the bar element.

According to a further aspect, the object is achieved by providing a wound occlusion method. The method comprises positioning the wound occlusion device in the wound and transforming the sealing element to the expanded configuration by the use of the release mechanism.

In a preferred embodiment of the method, the sealing element is covered by the sheath element, which may be delivered together with the ensemble of the base element and the sealing element into the wound.

In a further embodiment of the method, the sheath element retains the sealing element in its contracted configuration providing the release mechanism for the transformation to the expanded configuration by removing the sheath element. The expanded configuration of the sealing element may then be achieved by removing the sheath element. The sheath element may be removed by the use of handles coupled to the sheath element. In an embodiment of the method, the sheath element is removed by releasing the sheath coupling mechanism.

In an embodiment of the method, the retain apparatus is deployed using the deploy mechanism after positioning the wound occlusion device in the wound. The retain apparatus may then retain the wound occlusion device in the wound while removing elements of the wound occlusion device, as for example the sheath element.

The spatial dimensions, preferably the depth, of the wound may be determined by the use of the metering apparatus prior to the insertion of the wound occlusion device into the wound. The information about the spatial dimensions of the wound may then be used to choose a wound occlusion device of appropriate size out of a set of wound occlusion devices with different sizes and/or dimensions.

In another embodiment of the method, the wound occlusion device is positioned in the wound by introducing and positioning the ensemble of the bar element and the base element into and in the wound, guiding the ensemble of the carrier element and the sealing element onto the bar element, delivering of the ensemble of the carrier element and the sealing element into the wound by movement of the carrier element on the bar element, coupling of the ensemble of the carrier element and the sealing element to the base element by the use of the connector portions at the bottom portion of the carrier element and at the base element.

According to an embodiment of the method, the measurement scale on the bar element may be used to determine the spatial dimensions, preferably the depth, of the wound. The information about the spatial dimensions of the wound may then be used to choose a wound occlusion device and/or elements of the wound occlusion device of appropriate size out of a set of wound occlusion devices with different sizes and/or dimensions or out of a set of elements of the wound occlusion device with different sizes and/or dimensions.

In an embodiment of the method, the ensemble of the carrier element and the sealing element is covered by the sheath element, which may be delivered together with the ensemble of the carrier element and the sealing element into the wound.

In an embodiment of the method, the transformation of the sealing element to the expanded configuration is achieved by severing the strands coupling the sealing element to the top portion of the carrier element or to a portion of the bar element.

In another embodiment of the method, the sheath element retains the sealing element in its contracted configuration providing the release mechanism for the transformation to the expanded configuration by removing the sheath element.

After the application of the wound occlusion device and the transformation of the sealing element to its expanded configuration, the bar element may be removed by releasing the coupling to the base element. The ensemble of the sealing element in its expanded configuration and the base element may remain in the wound providing the occlusion of the wound.

In an embodiment of the method, the carrier element may be removed from the wound after the application of the wound occlusion device and the transformation of the sealing element to its expanded configuration by releasing the coupling of the carrier element to the base element. In an embodiment, the bottom ring of the carrier element may remain in the wound and the carrier element may be removed by releasing the coupling between the carrier element and the bottom ring. In addition, the bar element may be removed by releasing the coupling to the base element.

According to an embodiment of the method, manual force to hold the wound occlusion device may be applied to the bar element positioned in the wound during all steps of the application and removal procedure of elements of the wound occlusion device. When applied into the wound, the manual force on the bar element may provide a first occlusion of the wound in the contact region of the wound and the base element.

In an embodiment of the method, the sealing element in its expanded configuration and the base element may be removed, for example, in the hospital prior to any surgical action, by the addition of cold water or water containing ice, which may allow the sealing element to return to its contracted configuration due to the shape-memory material of the sealing element. In another embodiment, the sealing element in its expanded configuration and the base element may be removed by releasing the springs supporting the expanded configuration of the sealing element and/or by other surgical means.

According to a further embodiment, the wound occlusion device comprises a housing, wherein the carrier element, the sealing element and the base element are safely housed prior to use. The carrier element, the sealing element and the base element are insertable into the housing, which has preferably the shape of a cylinder with an open and a closed end. In the housing, the sealing element is kept in its contracted configuration.

According to a preferred embodiment, the base element and the sealing element are pushed out of the housing by the force of an ejection means, preferably a spring loaded element or an ejection spring, arranged within the housing.

The ejection means interacts preferably with the carrier element which can be pushed into the housing against the force of the ejection means thereby preloading the ejection means, for example an ejection spring. The carrier element is at least partially ejectable in the opposite direction out of the housing by the force of the ejection means.

The housing comprises, according to a preferred embodiment, a trigger mechanism which is arranged at least partially inside the housing, preferably at the closed end. The trigger mechanism is configured to trigger the ejection of the carrier element out of the housing.

Preferably, the trigger mechanism comprises at least one latching element and a trigger. The trigger mechanism comprises preferably a trigger spring. At least one latching elements is arranged on the carrier element and interacts with the trigger which is accessible at an outer surface of the housing. In a loaded and ready for use state, the carrier element is pushed into the housing against the force of the ejection means and kept in this position by the interaction of the at least one latching element and the trigger.

Preferably, the at least one latching element is a radial projection on the carrier element which is able to engage behind an undercut at the trigger, thereby blocking the movement of the carrier element along the longitudinal axis of the housing. By pushing the trigger, the user moves the undercut in radial direction away from the radial projection, thereby releasing the carrier element which is driven by the force of the ejection element in axial direction at least partially out of the open end of the housing, thereby pushing the base element and the sealing element out of the housing and into the wound.

The housing has preferably the overall shape of a big pen and protection caps are releasably mounted on one or both ends of the housing. A protection cap at the open end covers the opening and protects the base element and the sealing element from contamination. A protection cap at the closed end preferably covers the trigger and prevents unintentional release and ejection.

In order to avoid the latter, the trigger may be secured alternatively or in addition to the cap with a safety pin which has to be removed in order to action the trigger, for example by pressing or pulling.

According to further preferred embodiments, the wound occlusion device further comprises a block element, preferably arranged at the open end of the housing, which is engageable with the carrier element such that the ejection of the carrier element in axial direction out of the housing is limited.

According to further preferred embodiments, a locking mechanism locks the carrier element in the ejected position. This allows the user to push the base element together with the sealing element even deeper into the wound or to exert considerable pressure in axial direction if necessary, thereby ensuring that the carrier element is not pushed back into the housing.

After treating a wound, the locking mechanism can be released in order to allow the user to push back the carrier element into the housing after use, in particular when the wound occlusion device has to be loaded with a new base element together with a new sealing element.

In preferred embodiments of the wound occlusion devices with a housing, the front part of the housing with the open end is formed as a detachable sleeve. Said sleeve can be removed from the back part of the housing in order to make loading of the base element together with the sealing element easier. The sleeve is pushed in axial direction over the base element and the sealing element after connecting them with the carrier element and after bringing them into the ready for use state (carrier element pushed back and ejection means loaded).

The base element is preferably releasably attached or coupled to the end of the carrier element. Corresponding connector portions on the base element and the carrier element comprise for example simple plug in connections or suitable interlocking screw threads or male and female parts of bayonet joints.

In further preferred embodiments, the housing is equipped with a guiding rod which can be pushed in axial direction out of the housing in order to help the user of the wound occlusion device to position the device within the wound to be occluded. A handle interconnected with the guiding rod allows the user to move the guiding rod from a drawn-in position to an extended position, preferably with one finger, most preferred with a thumb. The guiding rod allows also to examine the depth of the wound and to identify the direction of the bullet-wound.

Advantageously, the overall application of the wound occlusion device requires well below 1 minute, providing a simple and an acute haemostatic treatment of the bleeding wound. The wound occlusion device may be an all-inclusive device without necessary additional equipment for the application like syringes, water etc., and can be applied by everybody including the injured person him- or herself.

BRIEF DESCRIPTION OF THE DRAWINGS

Embodiments of the present invention are explained in more detail according to the following drawings, which should not be considered limiting to the invention described in the appended claims.

FIGS. 11a-e show the steps of application of the wound occlusion device according to FIG. 9a for sealing wound W.

FIG. 12a shows the step of removal of the carrier element according to FIG. 11 and FIG. 12b the step of removal of the bar element.

FIG. 13a-b show steps of application of the wound occlusion device according to FIG. 3.

FIGS. 16a-c show consecutive steps of application of a further embodiment of the wound occlusion device according to the invention with a housing and a guiding rod in a sectional view along the longitudinal axis.

FIG. 18a-b show the two perspective views of the wound occlusion device according to FIG. 17a-b with the guiding rod in drawn-in position, the trigger without protection cap and the base element together with the sealing element in a released state in expanded configuration outside of the housing.

DETAILED DESCRIPTION OF THE EMBODIMENTS

A better understanding of the present invention may be obtained by the present detailed description which, when read in connection with the accompanying drawings, sets forth embodiments of the inventions described herein. The terminology used in the detailed description of the embodiments illustrated in the accompanying drawings is not intended to be limiting of the invention. It is to be understood that the drawings are schematic only and are not to scale. It should be understood that corresponding elements in the various figures are generally identified with corresponding reference numbers.

Figure 1:
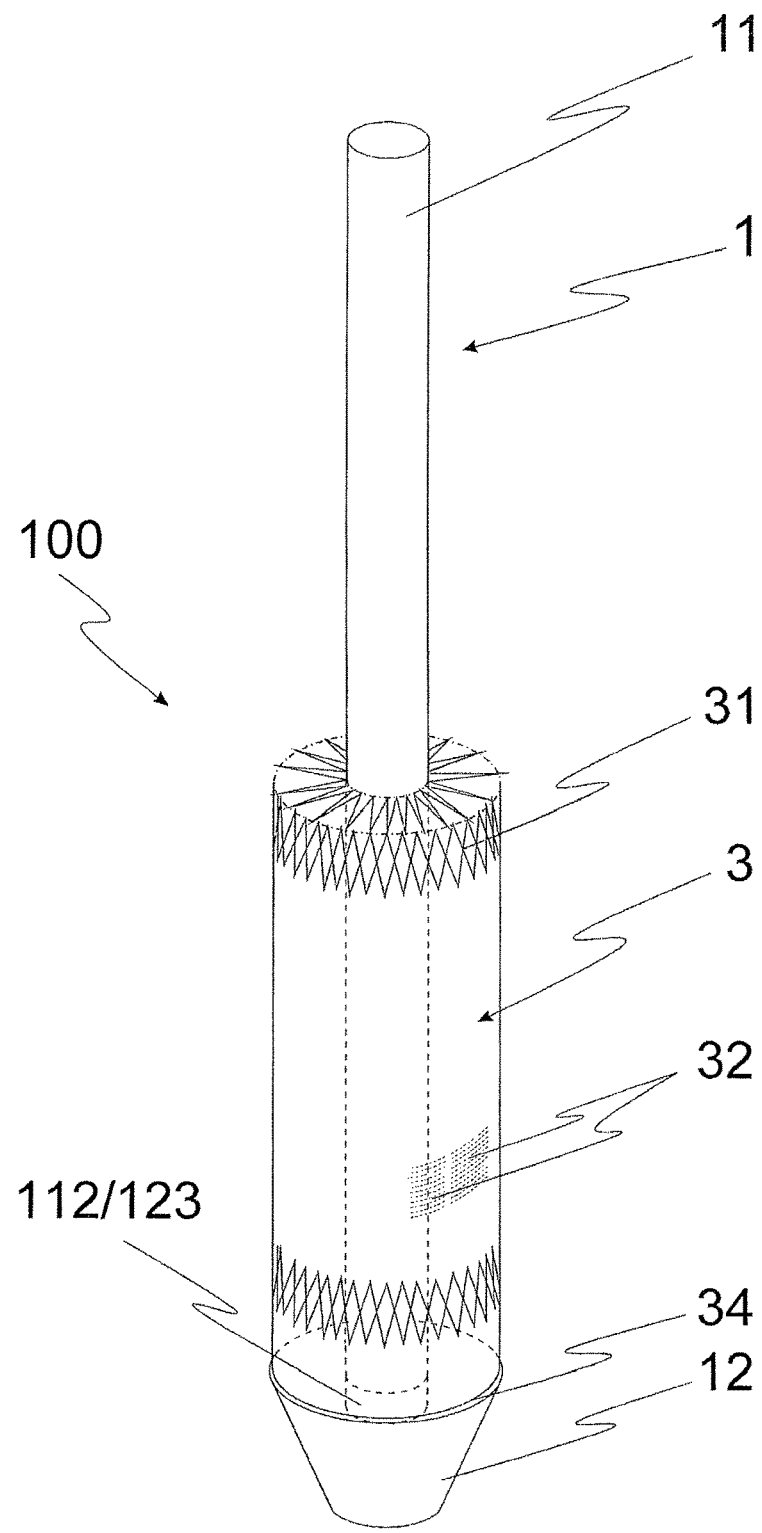
FIG. 1 a perspective view of an embodiment of a wound occlusion device comprising a base element, a bar element and a sealing element in the contracted configuration.

FIG. 1 is showing a perspective view of an embodiment of a wound occlusion device 100 comprising a bar element 11, a base element 12 and a sealing element 3. In the shown embodiment, the retain apparatus 1 comprises a bar element 11. The bar element 11 may be releasably coupled to the base element 12 through connector portions 112 (not shown in detail in FIG. 1) at the bottom portion of the bar element 11 and corresponding connector portions 123 at the base element 12. In the shown embodiment, the bar element 11 has a circular cross-section which, in various embodiments, may assume other shapes such as for example rectangular, hexagonal, or triangular cross-sections. In the shown embodiment, the base element 12 has a conical shape, roughly adapting to the shape of a wound W when first inserting the wound occlusion device 100 to the wound W. The sealing element 3, according to the shown embodiment, encompasses the bar element 11. Parts of the bar element 11 and the base element 12, which are covered by the sealing element 3, are depicted using dashed lines. Visible elements are depicted using solid lines. In the shown embodiment, the sealing element 3 is fixed to the base element 12 by fixing means 34 (not shown in detail in FIG. 1). In an embodiment, the sealing element may be releasably coupled to a portion of the bar element 11 by severable strands. The sealing element 3, according to the shown embodiment, comprises a frame element 31 which may comprise a wire braiding of a shape-memory material, such as Nitinol. The sealing element 3 may further comprise a layer element 32 which may be made of and/or covered by a blood-proof and/or water-proof material, which may be polytetrafluorethylen (PTFE). Preferably, the layer element 32 may be made of and/or covered by a haemostatic material supporting coagulation, such as Nu-Knit. The layer element 32 may, preferably, be covered by an antibacterial and/or antibiotic material, which may be GentaFleece. In the shown embodiment, the sealing element 3 is in the contracted configuration, where the sealing element 3 may be transformed to the expanded configuration by self-expansion relying on the shape-memory material or by a release mechanism (not shown in FIG. 1) which, in an embodiment, may comprise springs and/or severing the strands coupling the sealing element 3 to a portion of the bar element 11. The hatchings/patterns of the frame element 31 and the layer element 32 are shown only partially, but should be understood to indicate the material and/or the composition and/or the structure of the elements as a whole.

Figure 2:
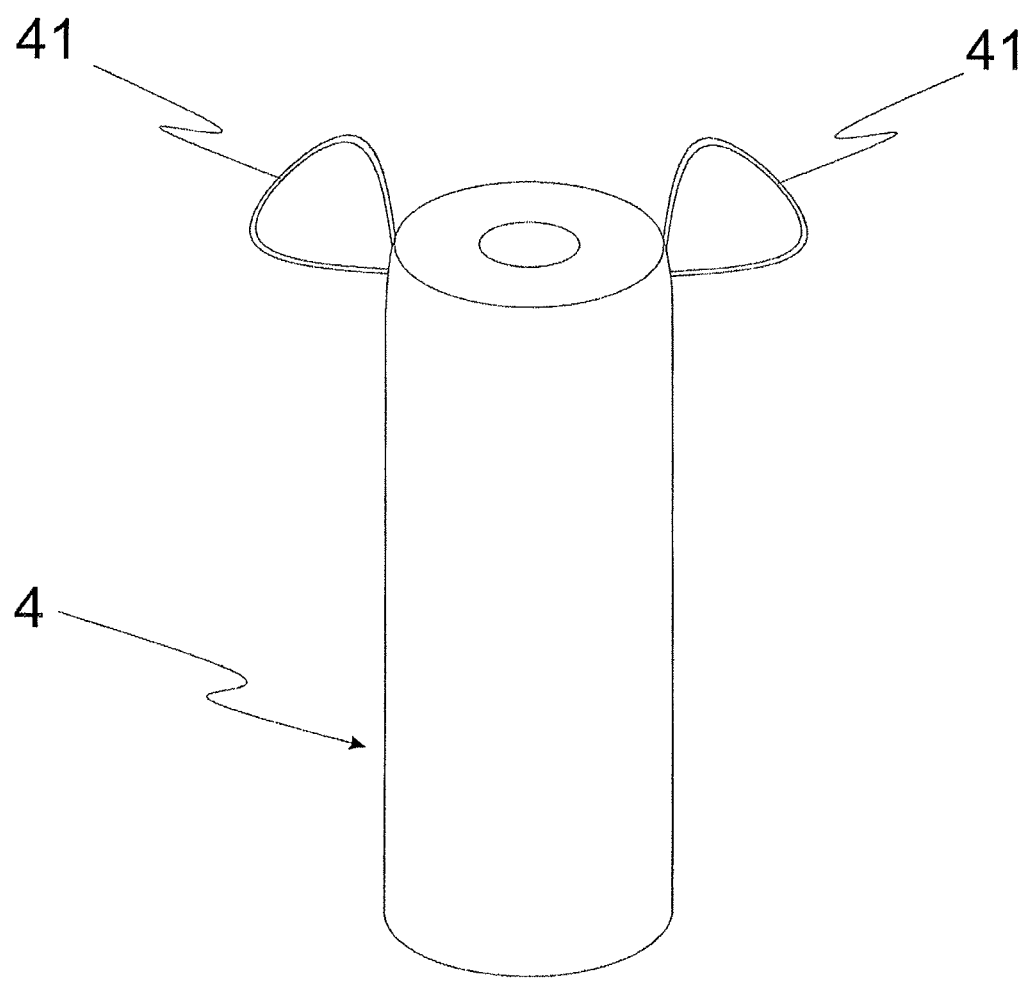
FIG. 2 a perspective view of an embodiment of a sheath element.

FIG. 2 is showing a perspective view of a sheath element 4. In an embodiment, the sheath element 4 may be made of a plastic material. The sheath element 4 may be formed such that the sealing element 3 according to FIG. 1 may be receivable in the sheath element 4. In the shown embodiment, the sheath element 4 comprises handles 41, which may allow to hold the sheath element 4 during the application and/or the removal of the wound occlusion device 100 or of elements of the wound occlusion device 100, such as for example the sheath element 4. The sheath element 4, according to the shown embodiment, may comprise a hole with a diameter equal or slightly larger than the bar element 11.

Figure 3:
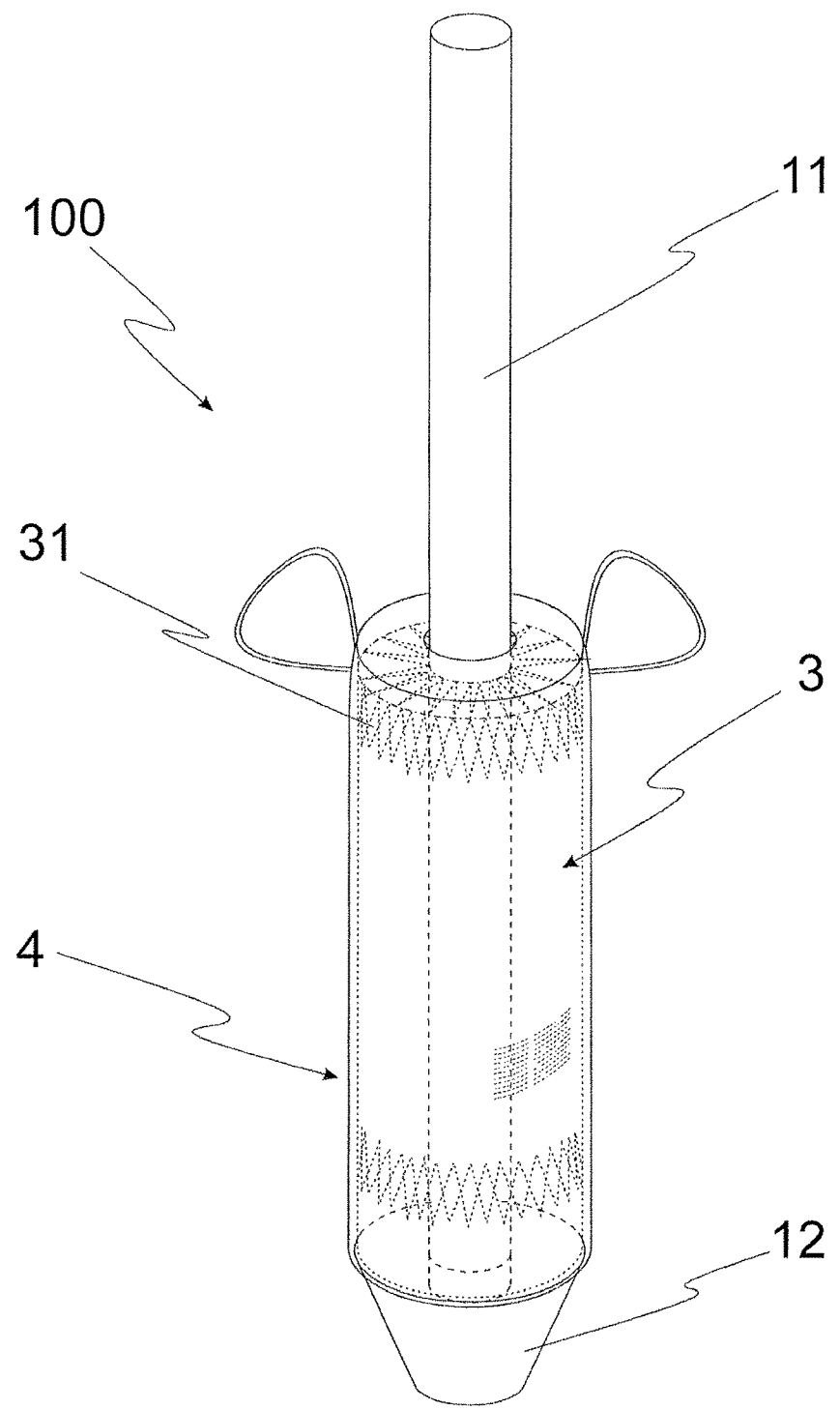
FIG. 3 a perspective view of a wound occlusion device comprising a base element, a bar element, a sealing element according to FIG. 1 and a sheath element according to FIG. 2 in an assembled state.

FIG. 3 is showing a wound occlusion device 100 according to FIG. 1, with the sheath element 4 according to FIG. 2, covering the sealing element 3. In an embodiment, the sheath element 4 may be releasably coupled to a portion of the bar element 11 by severable strands. In a preferred embodiment, the sheath element 4 may serve to retain the sealing element 3 in the contracted configuration, where upon removal of the sheath element 4 the sealing element 3 may transform to the expanded configuration by self-expansion relying on the shape-memory material of the frame element 31 and/or by other release mechanisms.

Figure 4:
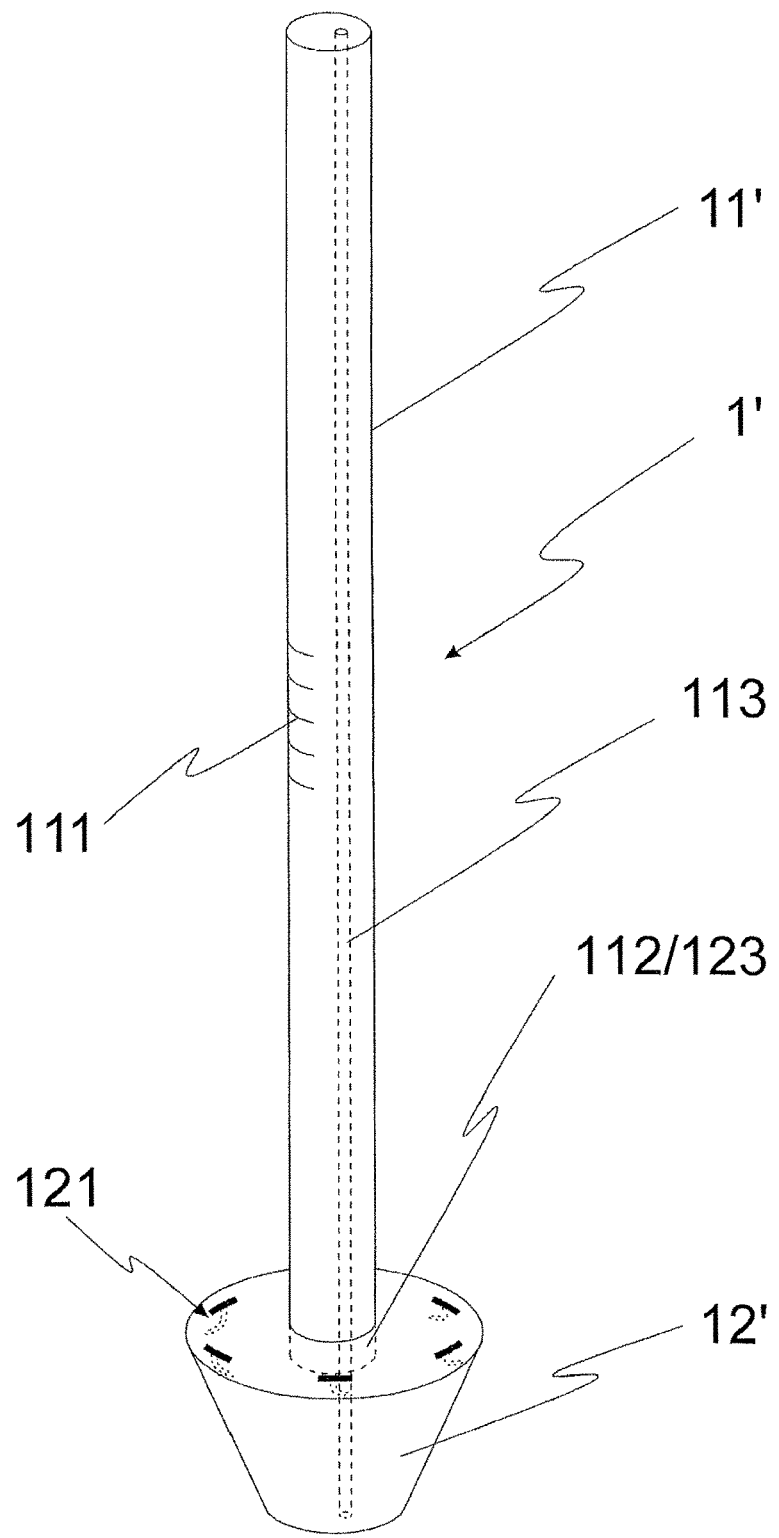
FIG. 4 a perspective view of a base element and a bar element according to a further embodiment.

Referring now to FIG. 4, there is shown a perspective view of another embodiment of a base element 12' and a retain apparatus 1' comprising a bar element 11'. The bar element 11' and the base element 12' of the shown embodiment may represent elements of another embodiment of the wound occlusion device 100', as the one shown as a whole in FIG. 9a. In the shown embodiment, the base element 12' has a conical shape, roughly adapting to the shape of a wound W when first inserting the wound occlusion device 100' to the wound W. The bar element 11' may comprise a metering apparatus 111, which, in an embodiment, may be a measurement scale shown as visible ticks 111. Shown is only a portion of the visible ticks 111 which, in different embodiments, may vary in position and/or extension over the bar element 11'. The metering apparatus 111, for example consisting of the visible ticks 111, may be used to determine the spatial dimensions of the wound W prior to the application of the wound occlusion device 100'. In the simplest case, the metering apparatus 111 may be used to determine at least the depth of the wound W. The information about the spatial dimensions of the wound W may be used to choose an appropriate wound occlusion device 100' among a set of wound occlusion devices 100' with different sizes and/or dimensions. The bar element 11' may be releasably coupled to the base element 12' through connector portions 112 (not shown in detail in FIG. 4) at the bottom portion of the bar element 11' and corresponding connector portions 123 at the base element 12'. The base element 12' may comprise connector portions 121 which, in an embodiment, may comprise male or female parts 121 of bayonet joints. In the shown embodiment, the bar element 11' has a circular cross-section which, in various embodiments, may assume other shapes such as for example rectangular, hexagonal, or triangular cross-sections. In the shown embodiment, the bar element 11' and the base element 12' comprises an additional dispensing means 113 comprising a cannula for the dispensing of drugs. It should be understood that the specific shape of the dispensing means 113 may vary from the shown embodiment and that the dispensing means 113 may be comprised also in other elements of the wound occlusion device 100', for example the carrier element 2 and/or the sealing element 3.

Figure 5:
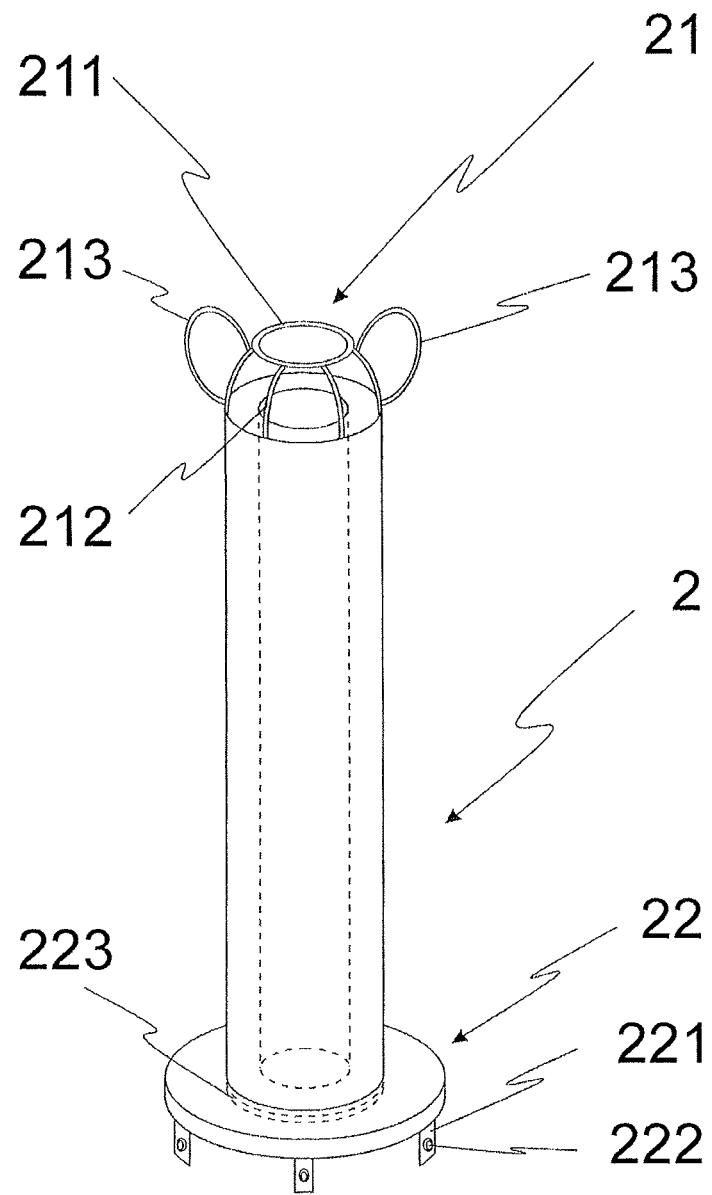
FIG. 5 a perspective view of a carrier element comprising a bottom ring with connector portions and a top ring assembly.

Referring now to FIG. 5, there is shown a perspective view of a carrier element 2 of tubular shape. In the shown embodiment, the diameter of the hole of the carrier element 2 of tubular shape matches or is slightly larger than the diameter of the bar element 11' according to FIG. 4. In other embodiments, the dimensions of the carrier element 2 may be formed such that the bar element 11' may be receivable in the carrier element 2 or, in other embodiments, such that the carrier element 2 is in any other way movable on the bar element 11'. In the shown embodiment, the carrier element 2 comprises a top ring assembly 21 comprising a top ring 211 and struts 212. Handles 213 may be attached to the struts 212 of the top ring assembly 21, and may allow to hold the carrier element 2 during application of the wound occlusion device 100' using fingers of a user of the wound occlusion device 100'. Handles 213 may also be used for the removal of the carrier element 2 from the wound W. The dimensions of the top ring assembly 21 may be formed such that the bar element 11' may be receivable through the top ring 211 of the top ring assembly 21. In the shown embodiment, the bottom portion of the carrier element 2 comprises a bottom ring 22, releasably coupled to the carrier element 2 by a screw joint 223 and through which the bar element 11' may be receivable. In other embodiments, the coupling between carrier element 2 and the bottom ring 22 may comprise different connector means, such as for example bayonet joints. In the shown embodiment, the bottom ring 22 comprises connector portions 221, which may comprise parts of bayonet joints, for example pins 222, matching the connector portions 121 of the base element 12' according to FIG. 4.

Figure 6:
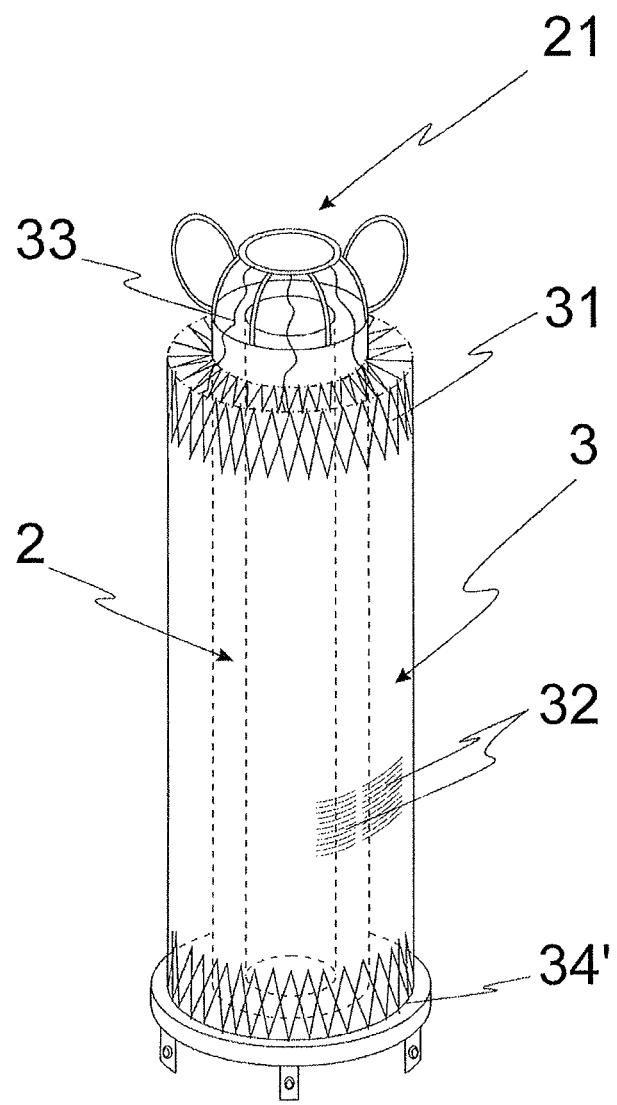
FIG. 6 a perspective view of a sealing element in the contracted configuration coupled to the carrier element according to FIG. 5.

FIG. 6 is showing the carrier element 2 according to FIG. 5, with an embodiment of a sealing element 3 releasably coupled to the top ring assembly 21 of the carrier element 2 by severable strands 33 and fixed to the bottom of the carrier element by fixing means 34' (not shown in detail in FIG. 6). In the shown embodiment, the sealing element 3 comprises a frame element 31 which may comprise a wire braiding of a shape-memory material, such as Nitinol. The sealing element 3 may further comprise a layer element 32 which may be made of and/or covered by a blood-proof and/or water-proof material, which may be polytetrafluorethylen (PTFE). Preferably, the layer element 32 may be made of and/or covered by a haemostatic material supporting coagulation, such as Nu-Knit. In the shown embodiment, the sealing element 3 is in the contracted configuration, where the sealing element 3 may be transformed to the expanded configuration by self-expansion relying on the shape-memory material or by a release mechanism (not shown in FIG. 6) which, in an embodiment, may comprise springs and/or severing the strands 33. The hatchings/patterns of the frame element 31 and the layer element 32 are shown only partially, but should be understood to indicate the material and/or the composition and/or the structure of the elements as a whole.

Figure 7:
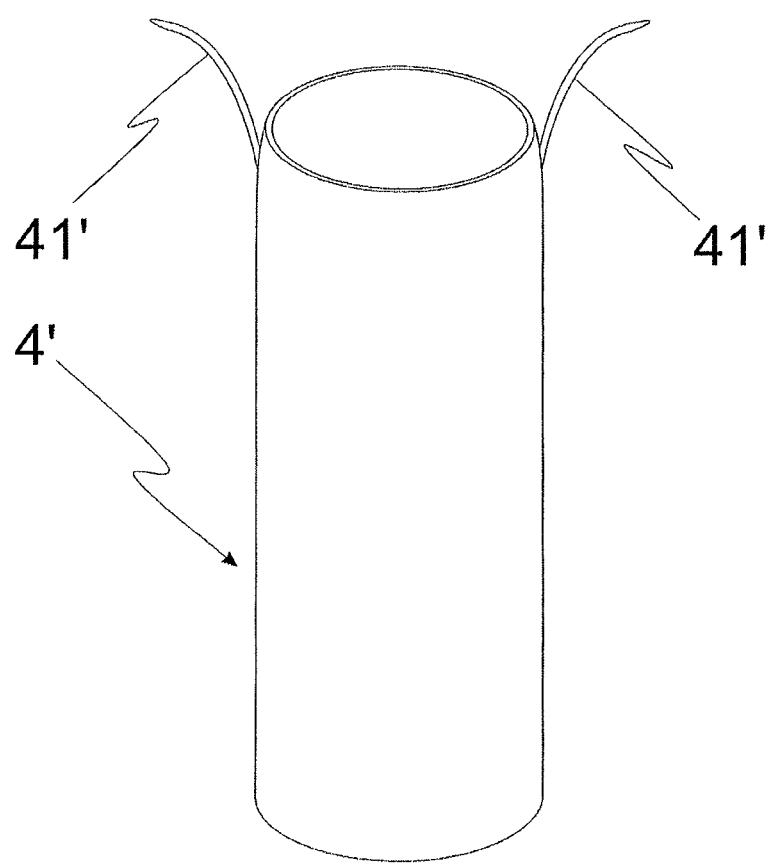
FIG. 7 a perspective view of an embodiment of a sheath element according to a further embodiment.

Referring now to FIG. 7, there is shown a perspective view of an embodiment of a sheath element 4' with handles 41'. In an embodiment, the sheath element 4' may be made of a plastic material. The sheath element 4' may be formed such that the ensemble of the carrier element 2 and the sealing element 3 according to FIG. 6 may be receivable in the sheath element 4'.

Figure 8:
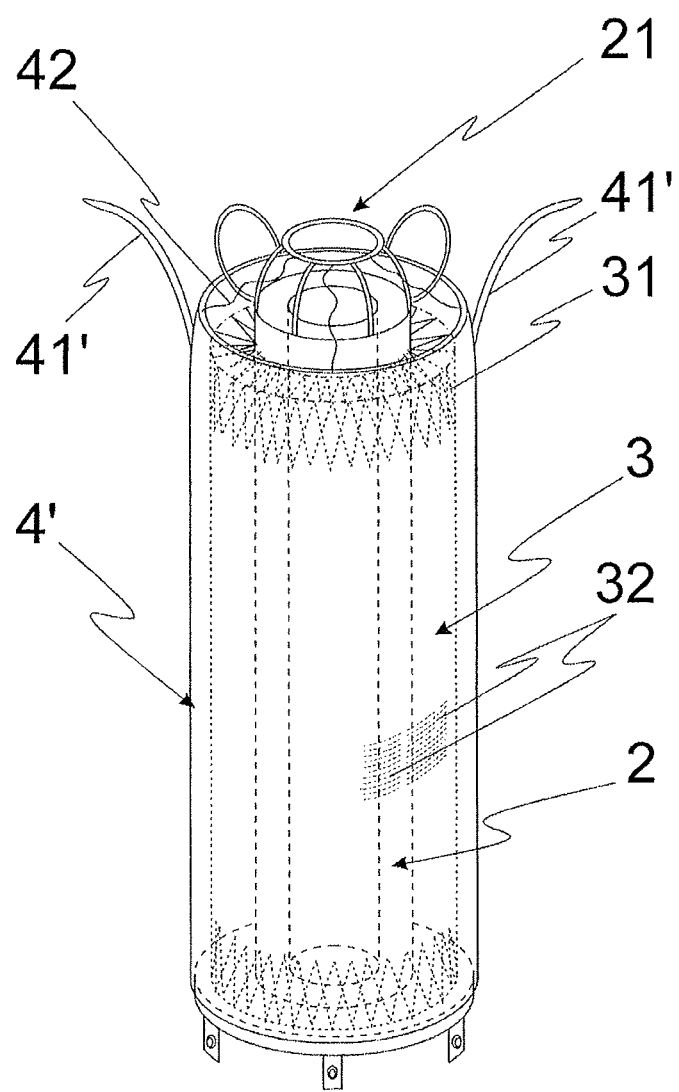
FIG. 8 the ensemble of the sealing element and the carrier element according to FIG. 6 covered by the sheath element according to FIG. 7.

FIG. 8 illustrates the sheath element 4' according to FIG. 7, covering the ensemble of the carrier element 2 and the sealing element 3 according to FIG. 6. In the shown embodiment, the sheath element 4' is releasably coupled to the top ring assembly 21 of the carrier element 2 by severable strands 42. In an embodiment, the sheath element 4' may serve to retain the sealing element 3 in the contracted configuration, where upon removal of the sheath element 4' the sealing element 3 may transform to the expanded configuration by self-expansion relying on the shape-memory material of the frame element 31 and/or by other release mechanisms.

Figure 9A:
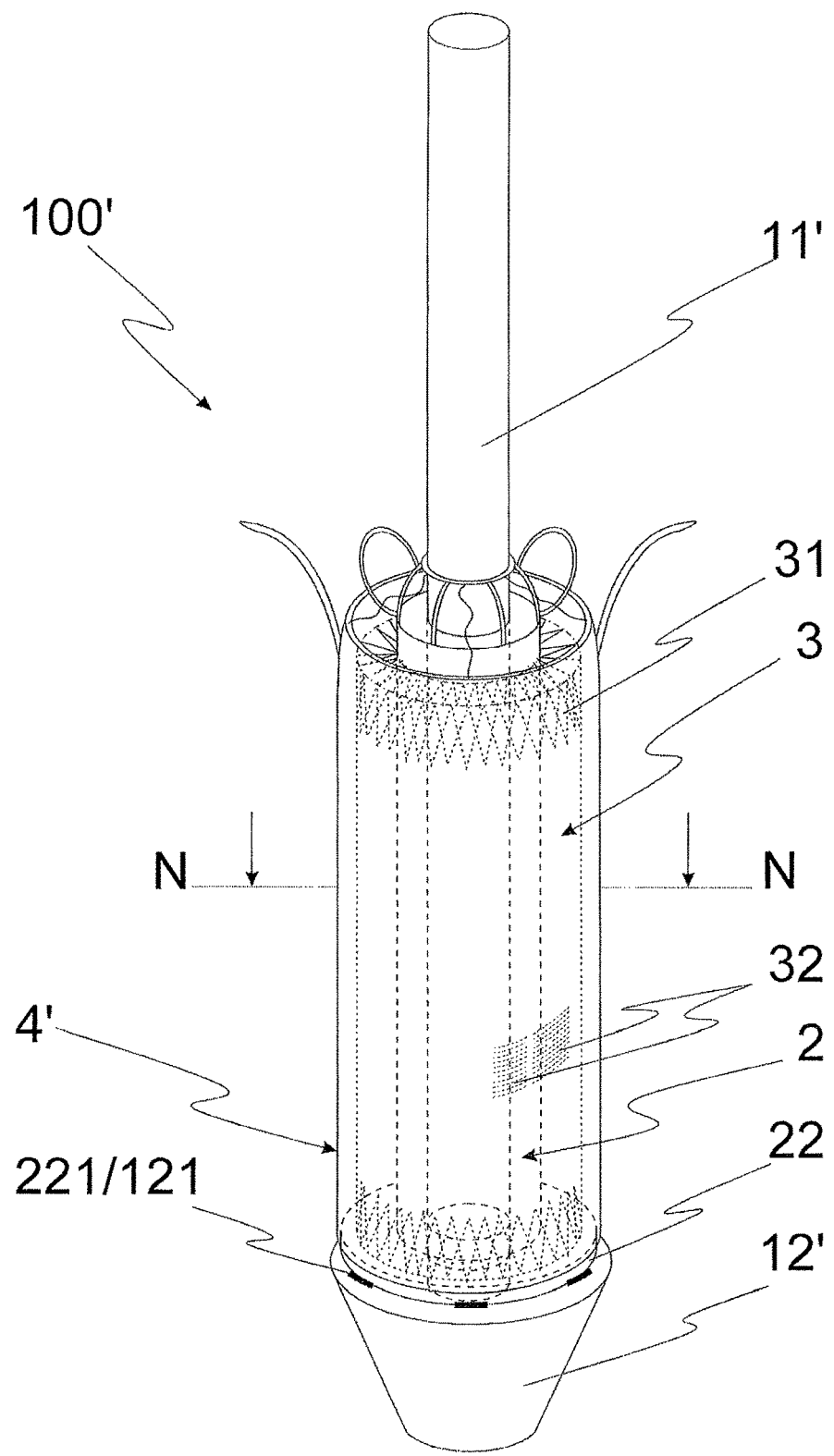
FIG. 9*a* shows in a perspective view an ensemble of the sealing element, the carrier element, and the sheath element according to FIG. 8 mounted on the bar element and the base element according to FIG. 4.

The ensemble of the carrier element 2 and the sealing element 3 covered by the sheath element 4', the base element 12', the bar element 11' received in the carrier element 2, forming together the wound occlusion device 100', is shown in a perspective view in FIG. 9a. In the shown embodiment, the bottom ring 22 of the carrier element 2 is coupled to the base element 12' by the connector portions 221 of the carrier element 2 and the connector portions 121 of the base element 12'.

Figure 9B:
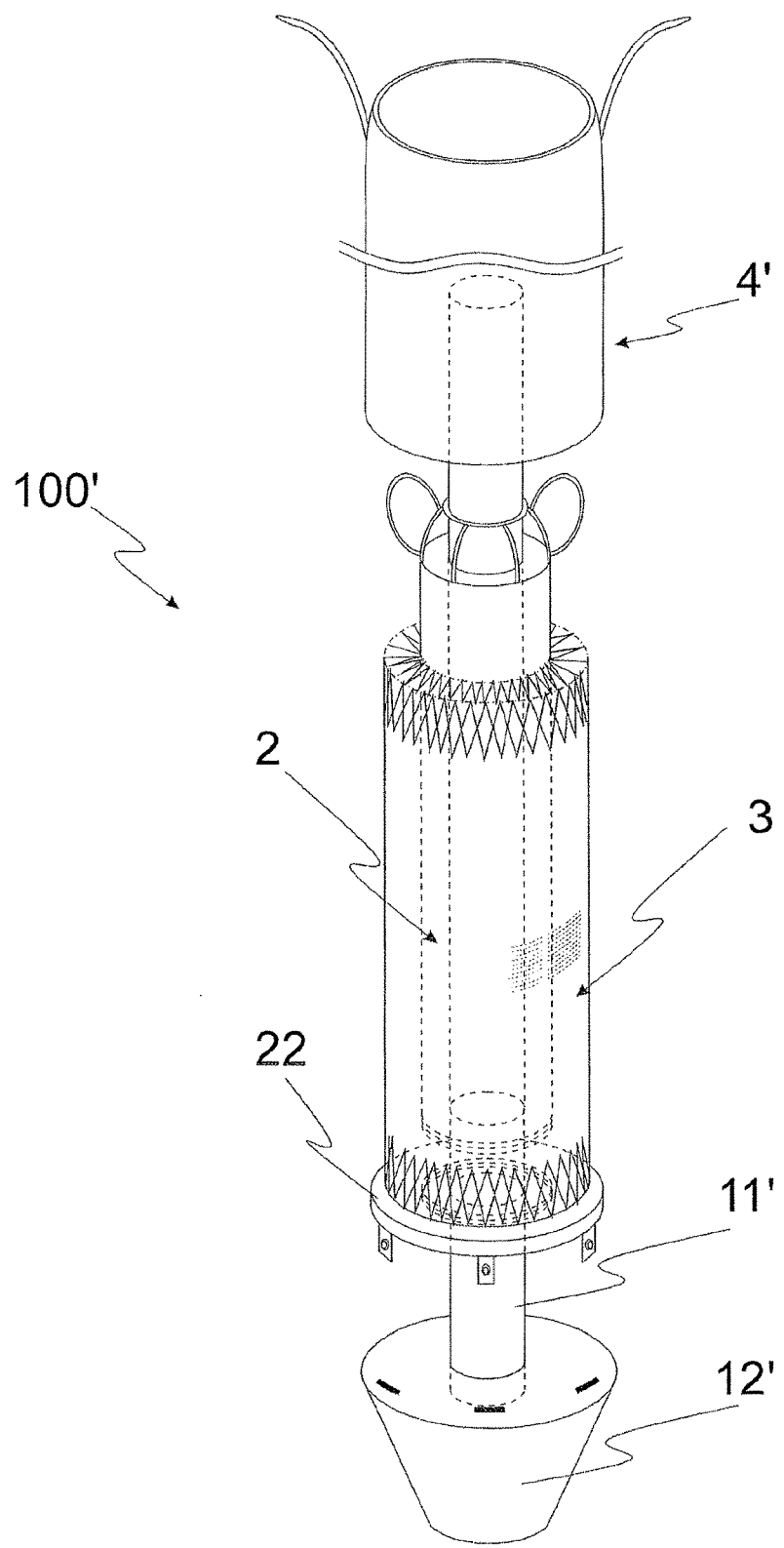
FIG. 9*b* shows in a partially disassembled view the wound occlusion device according to FIG. 9*a*, comprising the bar element and the base element according to FIG. 4, the carrier element according to FIG. 5, the sealing element according to FIG. 6, and the sheath element according to FIG. 7.

FIG. 9b is showing a disassembled view of the wound occlusion device 100' according to FIG. 9a, comprising the main parts: bar element 11', base element 12', carrier element 2, sealing element 3 and sheath element 4'. The wavy double line cutting the sheath element 4' illustrates the schematic reduction of the height of the sheath element 4' in FIG. 9b. In this view, the bottom ring 22 is shown as disconnected from the carrier element 2 and connected to the bottom of the sealing element 3.

Figure 10:
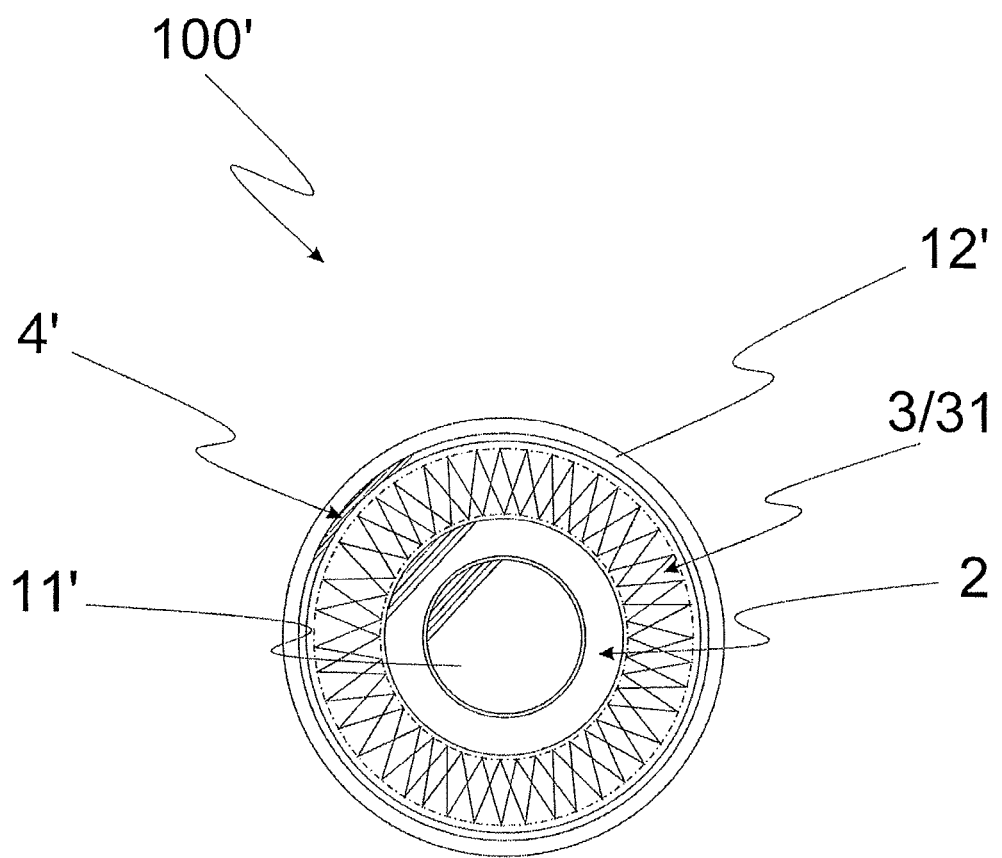
FIG. 10 shows a cross-section of the wound occlusion device of FIG. 9*a* according to the cut N-N.

Referring now to FIG. 10, there is shown a cross-section of the wound occlusion device 100' according to the cut N-N in FIG. 9a. The shown concentric assembly of the elements of the wound occlusion device 100' are as follows: In the centre is the bar element 11', followed by the carrier element 2 of tubular shape receiving the bar element 11' in the hole of the carrier element 2 of tubular shape, the sealing element 3 with the frame element 31 which may be, according to an embodiment, a wire braiding encompassing the carrier element 2, the sheath element 4' covering the ensemble of the carrier element 2 and the sealing element 3, and visible at the outermost circumference in FIG. 10, the base element 12'. Hatching of the cut bar element 11', carrier element 2 and sheath element 4' is shown only partially, but should be understood to indicate the material of the element as a whole. Not shown in FIG. 10 is the layer element 32 according to FIG. 6, which may cover the frame element 31 of the sealing element 3.

A method of the application of an embodiment of the wound occlusion device 100' according to FIG. 9a is shown in FIGS. 11a-11e. Referring to FIG. 11a, there is shown the ensemble of the base element 12' and the bar element 11', as applied into the wound W in the direction of the arrow. The ensemble of the carrier element 2 and the sealing element 3, covered by the sheath element 4', is delivered into the wound W by movement on the bar element 11', as shown in FIG. 11b. FIG. 11c is showing the wound occlusion device 100' as positioned in the wound W with the ensemble of the carrier element 2 and the sealing element 3, covered by the sheath element 4', coupled to the base element 12' by the connector portions 221 of the bottom ring 22 of the carrier element 2. The removal of the sheath element 4' after severing the strands 42 coupling the sheath element 4' to the top ring assembly 21 of the carrier element 2 is shown in FIG. 11d. The handles 41' may be used to hold the sheath element 4' while removing the sheath element 4'. The transformation of the sealing element 3 to the expanded configuration 3' in the direction of the arrows by the use of a release mechanism which, in an embodiment, may comprise severing the strands 33 coupling the sealing element 3 to the top ring assembly 21 of the carrier element 2, is shown in FIG. 11e. In a preferred embodiment, the expanded configuration 3' of the sealing element 3 may form a form-locked and/or force-locked connection with the wound W. The sealing element 3 may adapt to the shape of the wound W by exploiting the shape-memory material of the frame element 31 of the sealing element 3. In the expanded configuration 3', the wound occlusion device 100' may provide the occlusion of the wound W.

A method of the removal of elements of an embodiment of the wound occlusion device 100' according FIG. 9a is shown in FIGS. 12a and 12b. FIG. 12a illustrates the removal of the carrier element 2 along the bar element 11' (in the direction of the arrow) by releasing, in the shown embodiment, the screw joint 223. Referring now to FIG. 12b, there is shown a method to remove the bar element 11' by releasing, in the shown embodiment, the connector portions 112 of the bar element 11' and the connector portions 123 of the base element 12' (connector portions not shown in detail), leaving the base element 12' and the sealing element 3 in the expanded configuration 3' in the wound W. The wavy double line cutting the bar element 11' illustrates the schematic reduction of the height of the bar element 11' in FIG. 12b.

A method of the application of an embodiment of the wound occlusion device 100 according to FIG. 3 is shown in FIGS. 13a and 13b. Referring to FIG. 13a, the wound occlusion device 100 comprising the bar element 11, the base element 12, the sealing element 3 and the sheath element 4 is inserted into the wound W in the direction of the arrow. FIG. 13b illustrates the removal of the sheath element 4 using the handles 41 in the direction of the arrow while holding the wound occlusion device 100 comprising the bar element 11, the base element 12 and the sealing element 3 in the wound W. In the shown embodiment, the removal of the sheath element 4 triggers the release mechanism transforming the sealing element 3 into its expanded configuration 3'. The sealing element 3 in its expanded configuration 3' adapts to the wound W and provides the occlusion of the wound W by form-locked and/or force-locked connection with the wound W.

Figure 14:
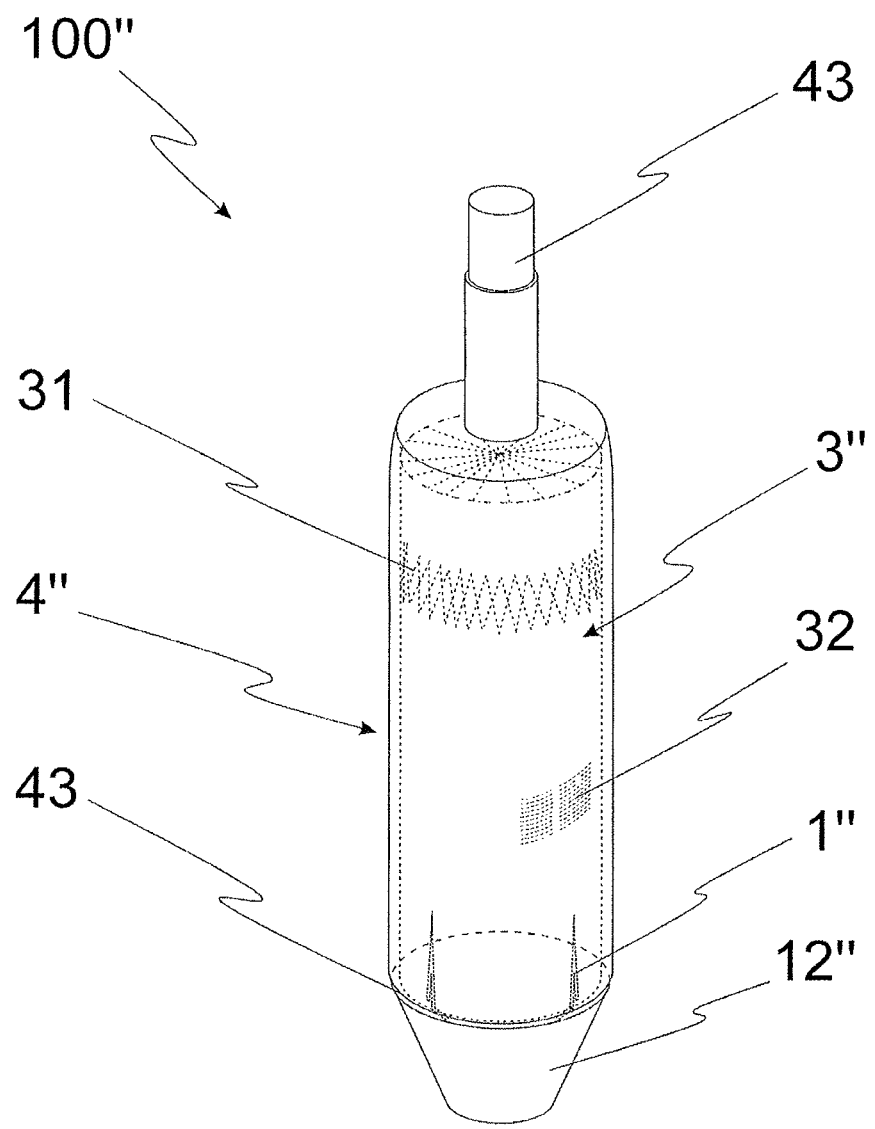
FIG. 14 shows in a perspective view a further embodiment of a wound occlusion device.

Referring now to FIG. 14, there is shown another embodiment of the wound occlusion device 100" comprising a base element 12", a sealing element 3", a sheath element 4" and a retain apparatus 1". The sealing element 3" may comprise a frame element 31 and a layer element 32 and may be fixed to the base element 12". The sealing element 3" may be retained in the contracted configuration by the sheath element 4". In the shown embodiment, the sheath element 4" comprises a releasable sheath coupling mechanism 43 coupling the sheath element 4" to the base element 12" (coupling to the base element 12" not shown in detail in FIG. 14). The coupling to the base element 12" may be released by a push-button 43 as part of the sheath coupling mechanism 43. The retain apparatus 1", in the shown embodiment, comprises hook elements 1" retained in a folded configuration by the sheath element 4".

Figure 15B:
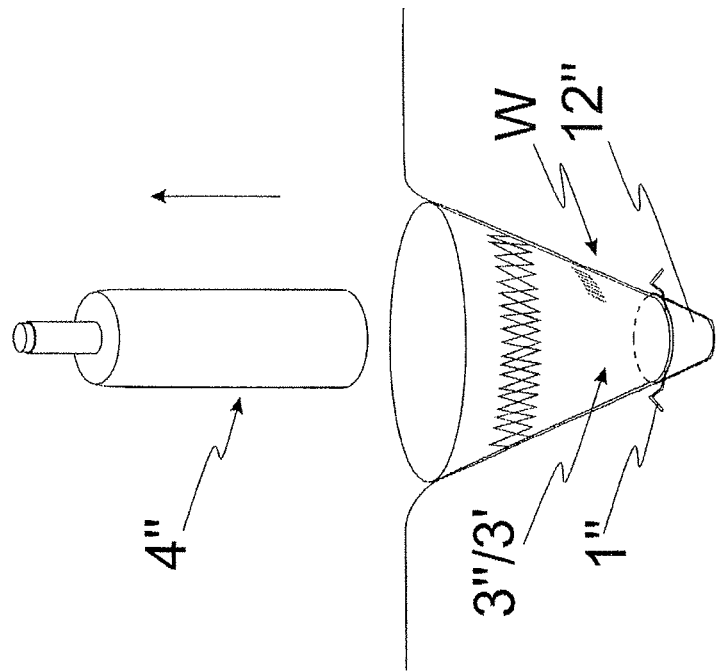
FIGS. 15a-b show consecutive steps of application of the wound occlusion device according to FIG. 14 in a wound W.
Figure 15A:
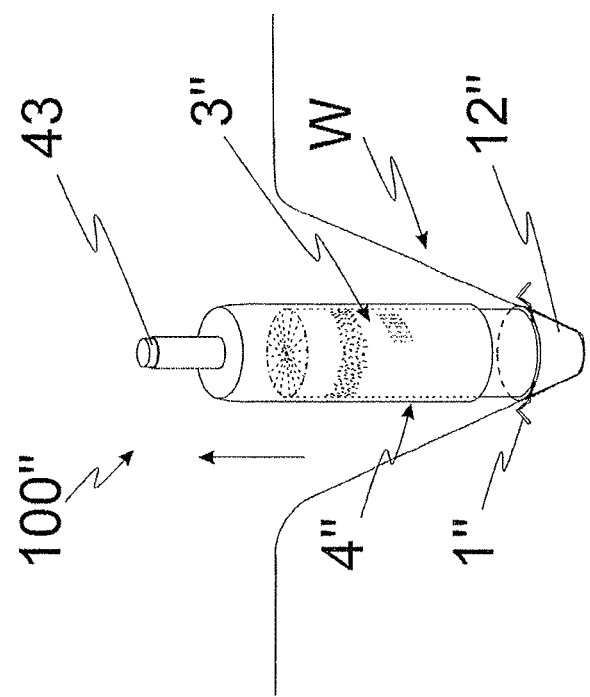
Figures 17A, 17B:
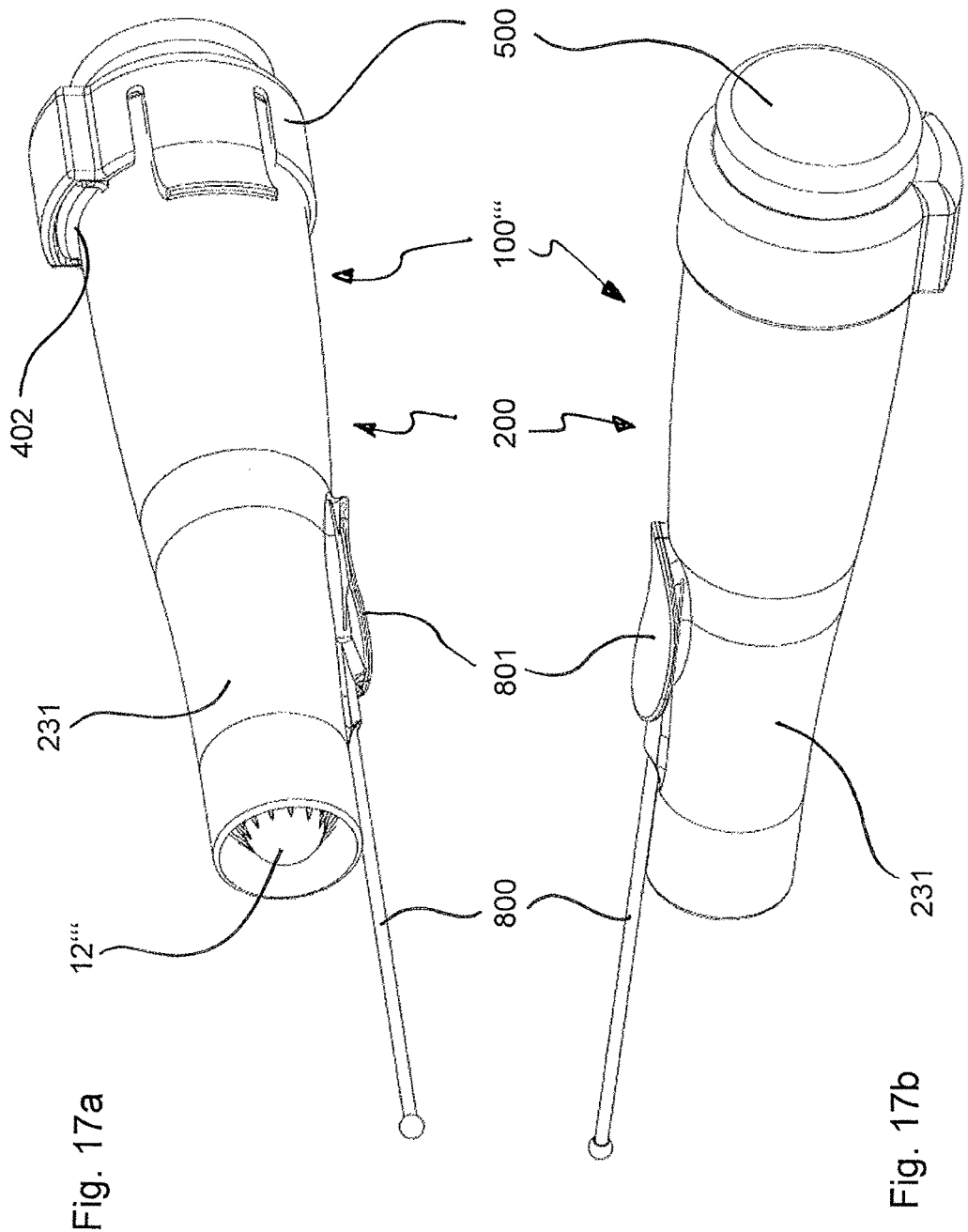
FIG. 17a-b show two perspective views of the wound occlusion device according to FIG. 16a with a guiding rod in extended position, a protection cap covering the trigger at a closed end of the housing and the base element together with the sealing element in a ready to use state within the housing.

FIGS. 15a and 15b illustrate an exemplary method of application of the wound occlusion device 100" according to FIG. 14. Referring to FIG. 15a, there is shown the wound occlusion device 100" inserted into the wound W and the sheath element 4" partially removed in the direction of the arrow after releasing the sheath coupling mechanism 43 using the push-button 43. In the shown embodiment, the hook elements 1" of the retain apparatus 1" are deployed due to the removal of the sheath element 4". The hook elements 1" may then hold the wound occlusion device 100" in the wound W during further steps of the removal of the sheath element 4". FIG. 15b illustrates the expanded configuration 3' of the sealing element 3" after complete removal of the sheath element 4". According to the shown embodiment, the sealing element 3" in its expanded configuration 3' and the base element 12" remain in the wound W providing the occlusion of the wound W.

FIGS. 16a-c show three consecutive steps of application of a further embodiment of the wound occlusion device 100''' according to the invention. In FIG. 16a the device 100''' comprises a housing 200, wherein the carrier element 2', the sealing element 3''' and the base element 12''' are safely housed prior to use. The carrier element 2', the sealing element 3''' and the base element 12''' are insertable into the housing 200, which has preferably the shape of a cylindrical pen with an open 202 and a closed end 201. In the housing 200 the sealing element 3''' is covered and kept in its contracted configuration by a removable sleeve 231.

In FIG. 16b the base element 12''' and the sealing element 3''' are pushed out of the housing 200 by the force of an ejection spring 300, arranged within the housing 200. The ejection spring 300 interacts not directly with the base element 12''' and the sealing element 3''' but with the carrier element 2' which is axially movable within the housing 200. The carrier element can be pushed against the force of the ejection spring 300 into the housing, thereby preloading the ejection spring 300. In use, the carrier element 2' is at least partially ejectable in the opposite direction out of the housing 200 by the force of the ejection spring thereby pushing the base element 12''' and the sealing element 3''' into the wound to be occluded.

In FIG. 16a a guiding rod 800 is shown in extended position projecting away from the open end 202 of the wound occlusion device 100'''. The guiding rod is slidably attached to the removable sleeve 231. In its extended position, the guiding rod 800 extends almost in parallel to the central longitudinal axis of the wound occlusion device 100''' and allows the user to explore the wound and to position the device in an optimal angle (preferably along the trajectory of the projectile) and in an optimal depth with respect to the wound. The guiding rod can be pushed back to a drawn-in position easily with a single finger, preferably a thumb, by a handle 801 attached to the guiding rod.

The housing 200 comprises a trigger mechanism 400 which is arranged at the closed end 201 of the housing 200. By pushing a trigger 402, the carrier element 2' and the base element 12''' and the sealing element 3''' attached to the carrier element 2' are ejected out of the housing 200 as shown in FIG. 16b.

As shown in FIG. 16a the trigger mechanism 400 comprises a latching element 401 positioned on the carrier element 2' and a trigger 402, which is held in a locking position by a trigger spring 403. The latching element 401 is projecting in radial direction from the carrier element 2' and interacts with the trigger 402 which is slidably housed in the housing and with one end accessible at an outer surface of the housing 200. In a loaded and ready for use state, the carrier element is pushed into the housing against the force of the ejection spring and kept in this position by the interaction of the latching element and the trigger.

The radial projection on the carrier element in form of the latching element 401 engages behind an undercut in the trigger 402 as shown in FIG. 16a, thereby blocking the movement of the carrier element 2' along the longitudinal axis out of the housing 200. By pushing the trigger 402 against the force of the trigger spring 403, the user moves the undercut of trigger 402 in radial direction away from the radial projection 401, thereby releasing the spring loaded carrier element 2' which is then driven by the force of the ejection spring 300 in axial direction at least partially out of the open end of the housing 200, thereby pushing the base element and the sealing element out of the housing and in use into the wound.

The housing 200 has the overall shape of a big pen and a protection cap 500 covers the closed end of the housing 200, thereby covering the trigger 402 and preventing unintentional release and ejection of the carrier element 2' and thereby the sealing element 3'' and the base element 12''. The cap 500 has to be removed before use in order to make the trigger accessible. The trigger 402 can be pushed with one finger, preferably a thumb. This allows using the wound occlusion device single handed.

As shown in FIG. 16b the cap 500 has been removed and the trigger 402 has been pushed. The sealing element 3''' and the base element 12''' are moved by the force of the ejection spring 300 acting on the carrier element 2' out of the housing 200 until the carrier element 2' is stopped in it's axial movement by a block element 600. The block element 600 is arranged towards the open end of the housing 200 and limits the ejection of the carrier element 2' in axial direction out of the housing 200 after the sealing element 3''' has been completely released from the housing and has reached its expanded configuration.

Prior to pushing the trigger 402, the guiding rod should be slid back in the drawn-in position in order to ensure that it is not blocking the expansion of the sealing element 3'''. However, the sealing element 3''' is flexible enough to ensure its correct expansion as soon as the extended guiding rod is drawn-in.

The base element 12''' is releasably coupled to the front end of the carrier element 2' as shown in FIGS. 16a and 16b. Corresponding connector portions 121' and 221' on the base element 12''' and the carrier element 2' respectively comprise a simple plug-in connection. In FIG. 16c the base element 12''' and the sealing element 3''' are released from the carrier element 2' after placement in a wound, which is not shown in FIG. 16c. Hooks 1''' keep the base element 12''' and the connected sealing element 3''' secured in the wound when the carrier element 2' is retracted together with the housing 200.

Figure 19:
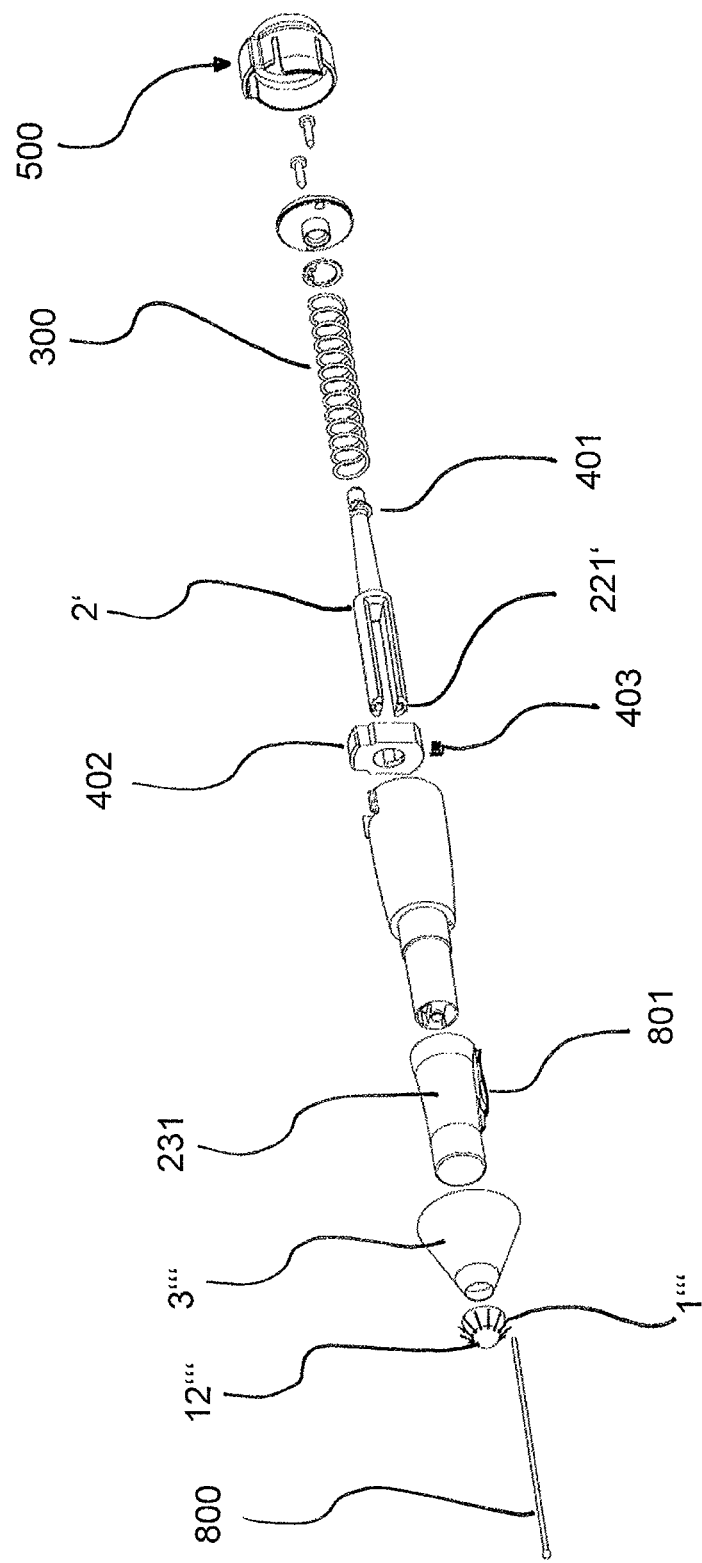
FIG. 19 shows an exploded view of the wound occlusion device according to FIGS. 16-18.

In the preferred embodiment shown in FIG. 16 and in an exploded view in FIG. 19, a front part of the housing 200 with the open end is formed as a detachable sleeve 231. Said sleeve 231 can be removed from the back part of the housing in order to make loading of the base element 12''' together with the sealing element 3''' easier. After loading, the sleeve 231 is pushed in axial direction over the base element 12''' and the sealing element 3''' already plugged on the carrier element 2' and after bringing them into the ready for use state. The removable sleeve makes it easier to load the base element 12''' with the hooks 1''' and the funnel shaped sealing element 3''' into the housing.

FIGS. 17a-b and 18a-b show the wound occlusion device 100''' according to FIG. 16 in two perspective views. In FIG. 16a-b the base element 12''' and the sealing element (which is not visible in the FIGS. 17a-b) are housed in the ready to use state in housing 200, the sealing element is in the contracted configuration. Guiding rod 800 is in extended position and protection cap 500 is covering the trigger 402 at the closed end of the housing. A user can probe the wound for depth and direction of the projectile with the guiding rod 800 prior to removal of the cap 500 and pulling the trigger 402.

FIG. 18a-b show two perspective views of the wound occlusion device 100''' after ejection of the base element 12''' and the sealing element 3''' with the guiding rod 800 in drawn-in position. The pushed trigger 402 lays open as the protection cap has been removed. The hooks 1''' of the base element 12''' and the sealing element 3''' are in their expanded configuration. In FIG. 18b parts of carrier element 2 carrying the base element 12''' are visible outside of the housing.

The hooks 1''' and the frame element of the sealing element 3''' are preferably made of Nitinol wire/mesh with an expansion temperature of 35 degrees centigrade. The sealing element preferably comprises a water and blood tight sealing membrane attached to the Nitinol mesh of the frame element. The sealing element shown in FIGS. 16 to 19 has a diameter of 10 mm at the connection to the base and of 38 mm at the opposite end. The height of the sealing element is shown in the Figures is 34 mm. Prior to loading in the housing, the sealing element 3''' the sealing element 3''' can be put in a freezer or in cold water in order so that the Nitinol mesh of the frame element already adopts its contracted shape. The use of the memory metal makes loading much easier.

The sizes of the wound occlusion devices according to the invention are adapted to the typical size of the wounds to be occluded. The force exerted by the sealing element to the wound in the expanded configuration is at least big enough to withstand the maximum hydrostatic pressure present in the biggest blood vessels.

Based on the disclosure above, the person skilled in the art can realize further types of ejection means and triggers in order to release the base element 12''' and the sealing element 3''' from the housing. The trigger may be for example located in a central position at the closed end of the housing.

The invention claimed is:

1. A wound occlusion device insertable into a wound W, comprising:
    a base element;
    a sealing element comprising a frame element and a layer element; and
    a release mechanism, wherein the sealing element is transformable between a contracted configuration and an expanded configuration by the release mechanism, the expanded configuration of the sealing element having a funnel-like shape adaptable to a shape of the wound W, forming a form-locked and/or force-locked connection with the wound W, the form-locked and/or force-locked connection of the sealing element with the wound W providing an occlusion function.

2. The wound occlusion device according to claim 1, wherein the frame element of the sealing element is selected from the group consisting of a wire coil, a wire mesh, and a wire braiding.

3. The wound occlusion device according to claim 1, wherein the frame element of the sealing element is made of or comprises a shape-memory material, preferably Nitinol.

4. The wound occlusion device according to claim 1, wherein the layer element is made of and/or covered by a material selected from the group consisting of a blood-proof material, a water-proof material, a haemostatic material, an antibacterial material, an antibiotic material, and combinations thereof.

5. The wound occlusion device according to claim 1, wherein the layer element is made of and/or covered by a material selected from the group consisting of polytetrafluoroethylene (PTFE), Nu-Knit, GentaFleece, and combinations thereof.

6. The wound occlusion device according to claim 1, further comprising a retain apparatus comprising hook elements and/or spring elements at a bottom portion of the wound occlusion device at the base element.

7. The wound occlusion device according to claim 1, wherein the base element comprises a skid-proof material.

8. The wound occlusion device according to claim 1, wherein the base element has a conical shape.

9. The wound occlusion device according to claim 1, wherein the sealing element is fixed to the base element.

10. The wound occlusion device according to claim 1, further comprising a carrier element.

11. The wound occlusion device according to claim 10, wherein the carrier element comprises connector portions at a bottom portion of the carrier element for releasably coupling with connector portions of the base element.

12. The wound occlusion device according to claim 10, further comprising a housing, wherein the carrier element, the sealing element and the base element are insertable into the housing, the housing having a shape of a cylinder with a closed end and an open end.

13. The wound occlusion device according to claim 12, further comprising an ejection spring arranged inside the housing, wherein the carrier element is insertable into the housing against a force of the ejection spring and ejectable out of the housing by the force of the ejection spring.

14. The wound occlusion device according to claim 13, further comprising a trigger mechanism arranged at least partially inside the housing preferably at the closed end, the trigger mechanism configured to trigger an ejection of the carrier element out of the housing.

15. The wound occlusion device according to claim 14, wherein the trigger mechanism comprises one or more latching elements and a trigger, one of the one or more latching elements being arranged at the carrier element, and the trigger being accessible at an outer surface of the housing.

16. The wound occlusion device according to claim 15, further comprising a cap mountable on the housing at the closed end and suitable to cover the trigger.

17. The wound occlusion device according to claim 12, further comprising a block element, preferably arranged at the open end of the housing, the block element engageable with the carrier element such that the ejection of the carrier element out of the housing is delimited.

18. The wound occlusion device according to claim 12, further comprising a locking mechanism configured to lock the carrier element in an ejected configuration.

19. The wound occlusion device according to claim 12, further comprising a guiding rod and a handle interconnected with the guiding rod, wherein the guiding rod is pushable into and/or out of the housing by the handle.

20. The wound occlusion device according to claim 1, further comprising a rod-like bar element comprising a retain apparatus.

21. The wound occlusion device according to claim 20, wherein the base element and the rod-like bar element are releasably coupled to each other by interacting connector portions, the interacting connector portions comprising screw elements or bayonet elements.

22. The wound occlusion device according to claim 20, wherein a carrier element is movable on the rod-like bar element, wherein the sealing element is releasably coupled to at least a portion of the carrier element and fixed to a bottom portion of the carrier element.

23. The wound occlusion device according to claim 22, further comprising carrier element connector portions positioned at a bottom ring of the carrier element for releasably coupling with base element connector portions, the carrier element connector portions selected from the group consisting of interlocking screw threads, male or female parts of bayonet joints, and other fitting means.

24. The wound occlusion device according to claim 20, wherein a length of the rod-like bar element is two times a length of the sealing element and/or of a sheath element.

25. The wound occlusion device according to claim 20, wherein the sealing element is fixed to a portion of the rod-like bar element.

26. The wound occlusion device according to claim 1, wherein the sealing element is covered in the contracted configuration by a removable sheath element including at least one handle positioned at a top portion of the sheath element.

27. The wound occlusion device according to claim 26, wherein the sheath element is releasably coupled to elements of the wound occlusion device by a sheath coupling mechanism.

28. The wound occlusion device according to claim 26, wherein the carrier element and the sealing element are covered by the removable sheath element.

29. The wound occlusion device according to claim 1, wherein the release mechanism of the sealing element comprises at least one spring and/or relies on self-expansion of the frame element and/or on precompression of the frame element.

30. The wound occlusion device according to claim 1, further comprising a metering apparatus comprising a measurement scale.

31. The wound occlusion device according to claim 30, wherein a bar element comprises the metering apparatus.

32. The wound occlusion device according to claim 1, further comprising a cannula coupled to the base element and/or the sealing element for dispensing fluids into the wound W.

33. A method for occluding a wound, comprising:
providing a wound occlusion device according to claim 1;
positioning the wound occlusion device in the wound W; and
transforming the sealing element from the contracted configuration to the expanded configuration using the release mechanism, thereby occluding wound W.

34. A wound occlusion device insertable into a wound W, comprising:
- a housing having a shape of a cylinder with a closed end and an open end;
- a carrier element, a sealing element, and a base element insertable into the housing, wherein the sealing element comprises a frame element and a layer element; and
- a release mechanism, wherein the sealing element is transformable between a contracted configuration and an expanded configuration by the release mechanism, the expanded configuration of the sealing element having a shape adaptable to a shape of the wound W, forming a form-locked and/or force-locked connection with the wound W, the form-locked and/or force-locked connection of the sealing element with the wound W providing an occlusion function.

35. A wound occlusion device insertable into a wound W, comprising:
- a base element;
- a rod-like bar element comprising a retain apparatus, wherein the base element and the rod-like bar element are releasably coupled to each other by interacting connector portions, the interacting connector portions comprising screw elements or bayonet elements;
- a sealing element comprising a frame element and a layer element; and
- a release mechanism, wherein the sealing element is transformable between a contracted configuration and an expanded configuration by the release mechanism, the expanded configuration of the sealing element having a shape adaptable to a shape of the wound W, forming a form-locked and/or force-locked connection with the wound W, the form-locked and/or force-locked connection of the sealing element with the wound W providing an occlusion function.

* * * * *